United States Patent [19]
Kirst et al.

[11] Patent Number: 4,920,103
[45] Date of Patent: Apr. 24, 1990

[54] MODIFICATIONS OF MYCINOSE AND 3-O-DEMETHYLMYCINOSE IN TYLOSIN-TYPE MACROLIDES

[75] Inventors: Herbert A. Kirst; James P. Leeds, both of Indianapolis, Ind.

[73] Assignee: Eli Lilly and Company, Indianapolis, Ind.

[21] Appl. No.: 912,891

[22] Filed: Sep. 29, 1986

[51] Int. Cl.$^5$ ...................... A61K 31/70; C07H 17/08
[52] U.S. Cl. ......................................... 514/30; 536/7.1
[58] Field of Search ............................ 514/30; 536/7.1

[56] References Cited

U.S. PATENT DOCUMENTS

| | | | |
|---|---|---|---|
| 4,366,309 | 12/1982 | Ganguly et al. | 536/7.1 |
| 4,415,730 | 11/1983 | Fujiwara et al. | 536/7.1 |
| 4,421,911 | 12/1983 | Fujiwara et al. | 536/7.1 |
| 4,436,729 | 3/1984 | Ganguly et al. | 424/180 |
| 4,443,436 | 4/1984 | Kirst et al. | 514/30 |
| 4,652,638 | 3/1987 | Fujiwara et al. | 536/7.1 |

FOREIGN PATENT DOCUMENTS 61-143394  7/1986  Japan .

OTHER PUBLICATIONS

H. A. Kirst, et al., "Structure-Activity Studies Among 16-Membered Macrolide Antibiotics Related to Tylosin", *J. Antibiotics* 35 (12), 1675–1682 (1982).

K. Kiyoshima et al., "Preparation of Antibacterial 4'''-Deoxy-4'''-Halo-and 4'''-Deoxytylosin Derivatives," *Chem. Abstr.* 107: 176412c (1987), Abstracting Japanese Patent Application JP 62,111,995.

Nagel et al., "Selective Cleavage of the Myucinose Sugar from the Macrolide Antibiotic Tylosin": a Unique Glycoside Scission, *J. Org. Chem.* 44 (12) 2050–2052 (1979).

*Primary Examiner*—John W. Rollins
*Assistant Examiner*—Elli Peselev
*Attorney, Agent, or Firm*—Nancy J. Harrison; Leroy Whitaker

[57] ABSTRACT

New 4'''-O-modified-20-modified tylosin and 4''-O-modified-20-modified-desmycosin and 4'-deoxydesmycosin derivatives of formula 1 have significant oral antibacterial activity. Compositions containing and methods of using these compounds are also provided.

31 Claims, No Drawings

MODIFICATIONS OF MYCINOSE AND 3-O-DEMETHYLMYCINOSE IN TYLOSIN-TYPE MACROLIDES

SUMMARY OF THE INVENTION

This invention relates to new derivatives of 20-modified tylosin-type macrolides which have formula 1:

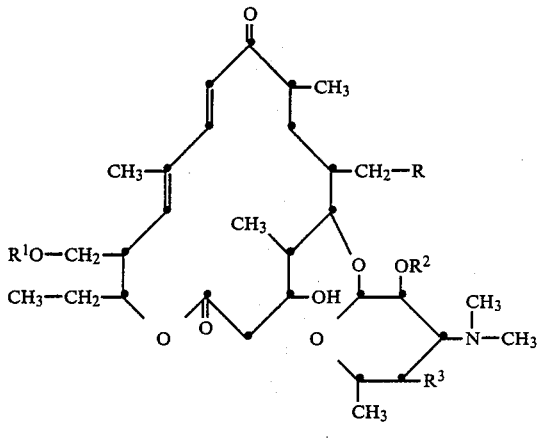

wherein
R is CH$_2$Z,

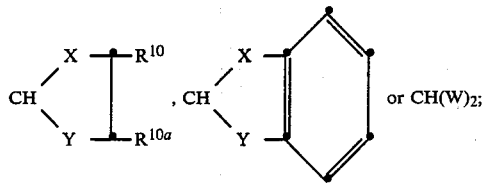 or CH(W)$_2$;

Z is hydrogen, halo, OR$^4$, SR$^5$, N$_3$ or NR$^6$R$^7$;
X and Y independently represent O, S, N—CH$_3$, N-phenyl or N-benzyl;
W is O(C$_1$-C$_4$-alkyl), S-phenyl or S-(R$^{11}$-substituted-phenyl);
R$^1$ is

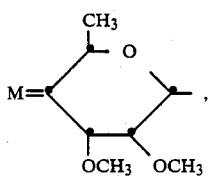 (a)

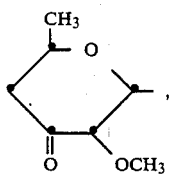 (b)

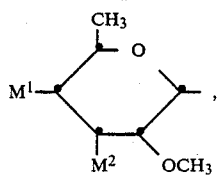 (c)

-continued

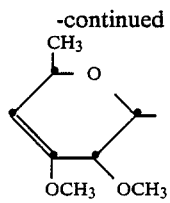 (d)

wherein
M is O, NOR$^{1a}$ or NH;
M$^1$ is hydrogen, halo, N$_3$, NR$^{12}$R$^{13}$, NH(C$_1$-C$_4$-alkanoyl), pyridinium, pyrrolyl, C$_1$-C$_4$-alkoxy, (C$_1$-C$_3$-alkoxy)-(C$_1$-C$_3$-alkoxy), OSO$_2$R$^{1b}$ or imidazolyl-thiocarbonyloxy;
M$^2$ is hydroxy or methoxy;
R$^{1a}$ is hydrogen, C$_1$-C$_4$-alkyl or C$_1$-C$_4$-alkyl having a C$_1$-C$_3$-alkoxy, C$_1$-C$_3$-alkoxy)-(C$_1$-C$_3$-alkoxy), NR$^8$R$^9$ or (R$^8$R$^9$N)-(C$_1$-C$_3$-alkoxy) substituent;
R$^{1b}$ is C$_1$-C$_4$-alkyl, halo-substituted-C$_1$-C$_4$-alkyl, phenyl, benzyl, or phenyl or benzyl, or phenyl or benzyl having from one to three C$_1$-C$_3$-alkyl, C$_1$-C$_3$-alkoxy or halo substituents;
R$^2$ is hydrogen, C$_1$-C$_5$-alkanoyl, halo-substituted-C$_1$-C$_5$-alkanoyl, or benzoyl, phenylacetyl or phenylpropionyl, each of which may have an R$^{11}$ substituent on the phenyl ring;
R$^3$ is hydrogen, OR$^2$ or

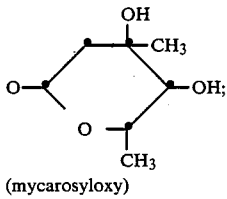
(mycarosyloxy)

R$^4$ is C$_1$-C$_4$-alkyl; C$_1$-C$_4$-alkanoyl; cyclohexyl; phenyl, benzyl, phenethyl or phenoxyethyl, each of which may have an R$^{11}$ substituent on the ring; or a heteroaryl group selected from pyridinyl, pyrimidinyl, pyridazinyl or pyrazinyl;
R$^5$ is C$_1$-C$_4$-alkyl; cyclohexyl; phenyl, benzyl or phenethyl, each of which may have an R$^{11}$ substituent on the phenyl ring; or a heteroaryl group selected from pyridinyl, tetrazolyl, oxazolyl or thiazolyl;
R$^6$ and R$^7$ independently are hydrogen, C$_1$-C$_8$-alkyl, or a group of the formula:

(CH$_2$)$_n$(Cyc)

where n is 0, 1 or 2, and Cyc is C$_3$-C$_8$-cycloalkyl, phenyl or R$^{11}$-substituted phenyl; or taken together with the adjacent nitrogen atom form a saturated or unsaturated heterocyclic monocyclic ring containing from 5 to 16 ring atoms or a bicyclic or tricyclic ring system containing from 8 to 20 ring atoms wherein one or more of the ring atoms may be substituted by C$_1$-C$_4$-alkyl, C$_1$-C$_4$-alkoxy, C$_1$-C$_4$-alkoxycarbonyl, hydroxy, C$_1$-C$_4$-alkanoyloxy, halo, NR$^8$R$^9$, phenyl or R$^{11}$-substituted phenyl;
R$^8$ and R$^9$ independently are C$_1$-C$_4$-alkyl or (CH$_2$)$_n$(Cyc); or taken together with the adjacent nitrogen atom form a saturated heterocyclic monocyclic ring containing from 5 to 8 ring atoms;

$R^{10}$ and $R^{10a}$ independently are hydrogen, methyl, phenyl, methoxycarbonyl, ethoxycarbonyl or phenoxycarbonyl; and $R^{11}$ is halo, $C_1$–$C_3$-alkyl, $C_1$–$C_3$-alkoxy, nitro or hydroxy; and $R^{12}$ and $R^{13}$ independently are hydrogen, cyanomethyl, $C_1$–$C_4$-alkyl or $(CH_2)_n(Cyc)$; or taken together with the adjacent nitrogen atom form a saturated heterocyclic monocyclic ring containing from 5 to 8 ring atoms;

and the acid addition salts of these compounds.

The compounds of this invention are useful as antibiotics and/or as intermediates to antibiotics. This invention also relates to pharmaceutical compositions comprising these compounds and to methods of treatment wherein these compounds or compositions are administered to obtain an antibiotic effect or to enhance growth promotion in animals.

DETAILED DESCRIPTION OF THE INVENTION

This invention relates to new antibiotics. In particular, this invention relates to a group of derivatives of the macrolide antibiotics tylosin, desmycosin, macrocin and lactenocin and to the acid addition salts of these derivatives. This invention also relates to methods of treating certain infections with, methods of promoting growth in animals with and pharmaceutical compositions comprising the specified derivatives and their pharmaceutically acceptable acid addition salts.

New improved antibiotics are continually in demand. In addition to antibiotics which are useful for treating human diseases, improved antibiotics are also needed in the veterinary field. Increased potency, expanded spectrum of bacterial inhibition, increased in vivo efficacy, and improved pharmaceutical properties (such as greater oral absorption, higher blood or tissue concentrations, longer body half-life, and more advantageous rate or route of excretion and rate or pattern of metabolism) continue to be goals for improved antibiotics.

A large number of derivatives of tylosin and related macrolides have been made. Unfortunately, many of these derivatives have been either less effective or no better than the parent compounds. One group of superior derivatives was obtained by reductive or protective chemical modification of the C-20 aldehyde group.

We have now discovered another series of derivatives with significant antibiotic activity and oral efficacy. In this series of compounds the 4'''-hydroxyl group of tylosin, the 3''' and/or 4'''-hydroxyl groups of macrocin or the analogous 4''-hydroxyl group of desmycosin or 3'' and/or 4''-hydroxyl groups of lactenocin have been modified. The novel macrolides of this invention are the compounds shown in formula 1.

Although no stereochemical assignments are indicated in the structures given herein, the stereochemistry is identical to that of the antibiotics from which the compounds are prepared, i.e. tylosin, macrocin, desmycosin and lactenocin, except at the 4''/4'''-position at which both epimers can be obtained.

The term "alkyl" means a hydrocarbon group containing the specified number of carbon atoms. Such groups can be straight, branched or cyclic and can be saturated or unsaturated. The term "cycloalkyl" means a cyclic hydrocarbon group containing the specified number of carbon atoms; such groups can also be saturated or unsaturated. By unsaturated is meant a hydrocarbon group containing double or triple bonds. The term "alkanoyl" refers to an acyl moiety derived from a carboxylic acid containing the specified number of carbon atoms. The term "halo-substituted" means that the specified alkyl or alkanoyl group bears one to three halo substituents. Examples of halo-substituted-alkyl groups are trifluoromethyl, 2,2,2-trichloroethyl and pentafluoroethyl; examples of halo-substituted alkanoyl groups are chloroacetyl, trichloroacetyl and trifluoroacetyl.

The term "protected-amino" means that the amino group is substituted by a suitable protecting group. Such a group must be compatible with the other functional groups in the macrolide such that it is readily removed under conditions which leave the rest of the macrolide intact. Appropriate amino-protecting groups are well known (see, for example, T. W. Greene, "Protective Groups in Organic Synthesis," John Wiley and Sons, New York, 1981, Chapter 7). Examples of suitable amino-protecting groups include carbamates such as t-butyl carbamate (BOC group), benzyl carbamate (CBZ group), methyl carbamate and substituted ethyl carbamate such as 2,2,2-trichloroethyl carbamate; amides such as formamide; imides such as phthalimide; N-aralkyl derivatives such as N-benzyl derivatives; and amino acetal derivatives such as N-methoxymethyl derivatives. One especially suitable amino-protecting group is the BOC group.

The term halo refers to a member of the group consisting of Cl, Br, I and F.

When Z is $NR^6R^7$ and the $NR^6R^7$ group is cyclic and unsaturated, representative groups are 1,2,3,6-tetrahydropyridin-1-yl; 1,2,3,4-tetrahydroquinolin-1-yl; 1,2,3,4-tetrahydroisoquinolin-2-yl; indol-1-yl; isoindol-2-yl; indolin-1-yl; isoindolin-2-yl; 2,3,4,5-tetrahydro-1H-1-benzazepin-1-yl; 2,3,4,5-tetrahydro-1H-2-benzazepin-2-yl; 2,3,4,5-tetrahydro-1H-3-benzazepin-3-yl; pyrrol-1-yl; 1H-azepin-1-yl; carbazol-9-yl; 9,10-dihydroacridin-10-yl; an dacridin-9-one-10-yl.

When Z is $NR^6R^7$ and the $NR^6R^7$ group is a saturated monocyclic ring, representative groups include pyrrolidin-1-yl, piperidin-1-yl, morpholin-4-yl, thiomorpholin-4-yl, piperazin-1-yl, hexahydroazepin-1-yl, octahydroazocin-1-yl, octahydro-1H-azonin-1-yl, and the like.

When Z is $NR^6R^7$ and the $NR^6R^7$ group is a saturated bicyclic or tricyclic ring, representative groups include decahydroquinolin-1-yl; decahydroisoquinolin-2-yl; decahydrocyclohepta[b]-pyrrol-1-yl; decahydrocyclohepta[c]-pyrrol-2-yl; decahydrocyclopent[[c]cazepin-2-yl; decahydrocyclopent[d]azepin-3-yl; an azabicycloheptanyl group such as 3-azabicyclo[3.2.0]heptan-3-yl; an azabicyclooctanyl group such as 6azabicyclo[3.2.1]octan-6-yl; an azabicyclononanyl group such as 3-azabicyclo[3.2.2]nonan-3-yl; an azabicyclodecanyl group such as 4-azabicyclo[5.3.0]decan-4-yl; an azatricyclo group such as 2-azatricyclo[6.2.2.2$^{3,6}$]tetradecan-2-yl or dodecahydrocarbazol-9-yl; and a spiro-fused system such as 1-azaspiro[4.5]decan-1-yl.

Representative groups when the $NR^6R^7$ group is a ring wherein one or more of the carbon atoms are substituted include 1,3,3-trimethyl-6-azabicyclo[3.2.1]octan-6-yl; 4-piperidinopiperidin-1-yl; 3,3,5-trimethylhexahydroazepin-1-yl; 4-phenylpiperidin-1-yl; 3,5-dimethylpiperidin-1-yl; N-methylpiperazinyl; and the like.

The formula 1 derivatives are prepared from tylosin, desmycosin, macrocin, lactenocin, 4'-deoxydesmycosin and 4'-deoxylactenocin via the C-20-modified derivatives of these compounds. Tylosin and desmycosin are described by R. L. Hamill et al. in U.S. Pat. No.

3,178,341, issued Apr. 13, 1965. Macrocin and lactenocin are described by Hamill et al. in U.S. Pat. No. 3,326,759, issued June 20, 1967. 4'-Deoxydesmycosin is prepared via procedures outlined in *J. Antibiotics* 34, 1381-1384 (1981). 4'-Deoxylactenocin is prepared by procedures described in our copending application entitled MODIFICATIONS OF 3-O-DEMETHYL-MYCINOSE IN MACROCIN AND LACTENOCIN, Ser. No. 06/912,890, filed herewith this even date. The structures of these starting materials are shown in formulas 2-7:

Method 2:
In this method, the aldehyde group of the starting antibiotic is reacted directly with the corresponding amine in the presence of a suitable reducing agent in an appropriate solvent until the desired product is formed. Sodium cyanoborohydride and sodium borohydride are examples of suitable reducing agents, and anhydrous methanol is a useful solvent for this reaction. The reaction may be carried out under a nitrogen atmosphere, but this is usually not required.

As Eddie V. P. Tao and Jeffrey T. Vicenzi describe

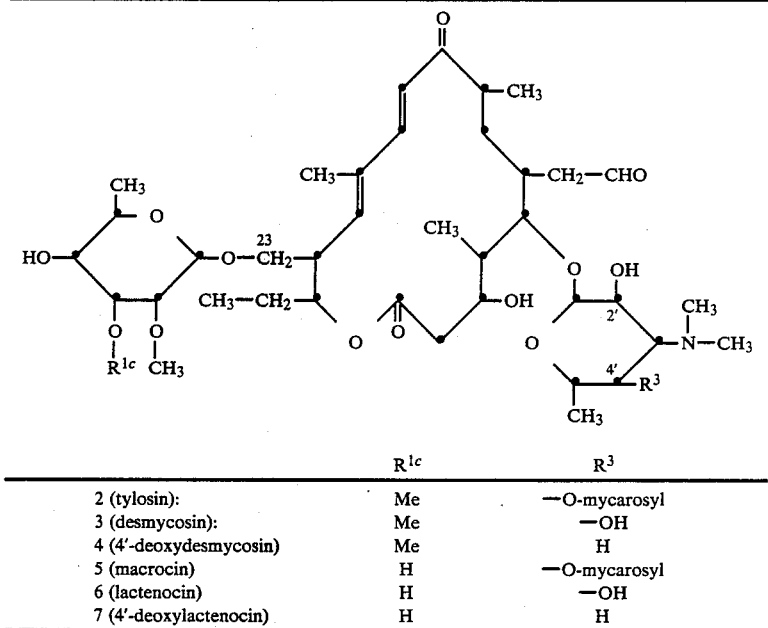

|  | $R^{1c}$ | $R^3$ |
|---|---|---|
| 2 (tylosin): | Me | —O-mycarosyl |
| 3 (desmycosin): | Me | —OH |
| 4 (4'-deoxydesmycosin) | Me | H |
| 5 (macrocin) | H | —O-mycarosyl |
| 6 (lactenocin) | H | —OH |
| 7 (4'-deoxylactenocin) | H | H |

The first step in preparing the formula 1 compounds is to modify compounds 2-E,uns/7/ at the C-20 position, using procedures in the art [see, for example, U.S. Pat. Nos. 4,443,436 and 4,440,759; Matsubara et al., *Chem. Pharm. Bull* 30(1), 97-110 (1982); Omura et al., in *J. Antibiotics* 37(9), 1007-1015 (1984); and the copending application of Manuel Debono and Herbert A. Kirst, application Ser. No. 517,136, filed July 25, 1983]. The C-20 modified cyclic amino derivatives of the copending application are prepared by two general methods.

Method 1:
In this method, the aldehyde group of the starting antibiotic is first reduced to give the corresponding 20-dihydro compound. The C-20 hydroxyl group in this compound is then converted to a leaving group suitable for displacement reactions by one of two methods. In one method the C-20 hydroxyl group is converted to the trifluoromethanesulfonyloxy (triflate) group, which may be further converted to another leaving group such as iodo, if desired. In the other method, which can be used with desmycosin, lactenocin or their 4'-deoxy-derivatives, the iodo derivative is directly formed by addition of iodine (which may be dissolved in a suitable solvent such as dimethylformamide) to a solution of the 20-dihydro derivative and triphenylphosphine under nitrogen.

The leaving group at C-20 (iodo, triflate, etc.) is then displaced by reaction with the appropriate amine in a suitable solvent, such as acetonitrile, until formation of the desired 20-modified derivative is complete in U.S. patent application Ser. No. 846,446, filed Mar. 31, 1986, entitled IMPROVED PROCESS FOR PREPARING MACROLIDE DERIVATIVES, formic acid can also be used as the reducing agent.

The C-20-modified derivatives of desmycosin and lactenocin can also be prepared by acidic hydrolysis of mycarose from the corresponding C-20-modified derivatives of tylosin and macrocin, respectively. Procedures for the acidic hydrolysis of mycarose from tylosin or macrocin to form desmycosin or lactenocin are well known.

In many cases, the C-20-modified derivative of desmycosin or lactenocin can be converted to the C-20-modified-4'-deoxy analog by procedures similar to those used to prepare 4'-deoxydesmycosin from desmycosin.

The second step in preparing the formula E,uns/1/ compounds is to protect the hydroxyl groups at the 2' or 2' and 4'-positions. The 2'-mono-esters of the C-20modified tylosin, macrocin, 4'-deoxydesmycosin or 4'-deoxylactenocin and the 2',4'-diesters of C-20-modified desmycosin or lactenocin are prepared by esterifying the C-20-modified compound on the appropriate hydroxyl groups by treatment with acylating agents, using standard methods well exemplified in the art (see, for example, U.S. Pat. No. 4,443,436).

To prepare the compounds wherein $R^1$ is an (a) group and M is oxygen, the next step is to oxidize the 2'- and-/or 4'-protected C-20-modified starting material at the 4-position of the mycinose moiety to give a keto group (the 1a keto derivatives). This hydroxyl group is at the 4'''-position in tylosin, but is at the 4''-position in desmycosin and 4'-deoxydesmycosin. The oxidation can be carried out by a variety of procedures, such as (1) a Moffatt oxidation using dimethyl sulfoxide (DMSO), an acid catalyst and a dehydrating agent, and (2) oxalyl chloride-DMSO (Swern's reagent). A preferred oxidizing reagent for this reaction is N-chlorosuccinimide-dimethyl sulfide (Corey-Kim reagent).

The formula 1a a compounds wherein M is NOR$^{1a}$ (the 1 a oximes) are prepared by reacting the corresponding 1a a keto derivative with the appropriate hydroxylamine derivative, e.g. NH$_2$OR$^{1a}$, using conditions known in the art.

The formula 1a compounds wherein M is NH (the 1a a imines) can be prepared by reduction of the 1a a oximes (R$^{1a}$=H) using aqueous titanium trichloride and methanol. The 1a imines are relatively unstable to hydrolysis, but are useful intermediates to the 1c compounds wherein M$^1$ is amino (the 1c amino compounds). The intermediate imine is preferably not isolated, but is converted in situ to the 1c amino compound by reducing agents such as borohydride reagents. Another preferred way to make the 1c amino compounds is by reducing the 1a oxime in a single step with a complex reducing agent such as titanium trichloride/sodium cyanoborohydride in a solvent such as methanol.

The formula 1c compounds wherein M$^1$ is OSO$_2$R$^{1b}$ are formed by treating the 2'- and/or 4'-hydroxy-protected C-20-modified starting antibiotic with the appropriate sulfonyl chloride or anhydride to give the corresponding 4''- or 4'''-OSO$_2$R$^{1b}$ derivative. For example, the triflates are prepared by standard methods using trifluoromethanesulfonic anhydride and pyridine in a solvent such as dichloromethane. The 4''- or 4'''-O-triflates of the 2'- and/or 4'-hydroxy-protected C-20-modified starting antibiotics are especially useful as intermediates for further chemical modification.

The triflate can be reacted with a base such as a hindered amine, e.g. 1,8-diazabicyclo[5.4.0]undec-7-ene (DBU) in a solvent such as THF to give, when M$^2$=hydroxy, the formula 1b derivatives (the 1b keto compounds) When M$^2$=methoxy, the formula 1d derivatives are prepared by this procedure. Another method for making the 1b keto compounds is via the corresponding 1d derivatives, which can be hydrolyzed by methods well known in the art, such as acid-catalyzed hydrolysis, in solvents such as aqueous MeOH to give 1b keto compounds.

The formula 1c compounds wherein M$^1$ is halo, N$_3$, NH$_2$, pyridinium, pyrrolyl, C$_1$-C$_4$-alkoxy or (C$_1$-C$_3$-alkoxy)-(C$_1$-C$_3$-alkoxy) can be prepared from the 4''- or 4'''-O-triflate intermediate by solvolytic or nucleophilic substitution (Sn1 or Sn2) reactions, using standard procedures. The stereochemistry obtained at 4''/4''' is predominantly with retention of configuration in most cases, but the epimer is sometimes observed. Compounds in which M$^1$=N$_3$ can be reduced to those in which M$^1$=NH$_2$ using known reagents, such as, for example, triphenyl phosphine in aqueous tetrahydrofuran.

The 1c compounds wherein M$^1$=but does not =NH$_2$ are prepared from the 1c compounds wherein M$^1$=NH$_2$ by reductive amination. The compounds wherein M$^1$=NH(C$_1$-C$_4$-alkanoyl) are also prepared from the 1c compounds wherein M$^1$=NH$_2$ by selective acylation.

The 1c compounds wherein M$^1$=hydrogen are prepared by Bu$_3$SnH reduction of the 1c compounds wherein M$^1$=imidazolyl-thiocarbonyloxy.

The 1c compounds wherein

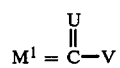

can be prepared by acylation as described in our co-pending application entitled NEW ACYL DERIVATIVES OF 20-MODIFIED TYLOSIN AND DESMYCOSIN COMPOUNDS, Ser. No. 06/912,880, filed herewith this even date.

In the final step, selective deesterification of the 2' and/or 4'-positions using standard methanolysis conditions provides the desired formula 1 compounds wherein R$^2$ is hydrogen (see U.S. Pat. No. 4,443,436 for suitable conditions).

The formula 1 compounds can form acid addition salts. These salts are also useful as antibiotics and are a part of this invention. In another aspect, the salts are useful as intermediates, for example, for separating and purifying the derivatives. In addition, the salts have an improved solubility in water.

Representative suitable salts include those salts formed by standard reactions with both organic and inorganic acids such as, for example, sulfuric, hydrochloric, phosphoric, acetic, succinic, citric, lactic, maleic, fumaric, palmitic, cholic, pamoic, mucic, D-glutamic, d-camphoric, glutaric, glycolic, phthalic, tartaric, formic, lauric, stearic, salicylic, methanesulfonic, benzenesulfonic, sorbic, picric, benzoic, cinnamic, and like acids.

Pharmaceutically acceptable acid addition salts are an especially preferred group of salts of this invention.

Illustrative formula 1 compounds are listed in Table I.

TABLE I

Illustrative Formula 1 Derivatives

| Compound No. | R | R$^1$ Group | Substituents | R$^2$ | R$^3$ |
|---|---|---|---|---|---|
| 1 | CH$_2$OPh | (a) | M = O | Ac | OAc |
| 2 | '' | '' | '' | H | OH |
| 3 | '' | '' | M = NOH | Ac | OAc |
| 4 | '' | '' | '' | H | OH |
| 5 | '' | '' | M = NOMe | Ac | OAc |
| 6 | '' | '' | M = NOMe (syn to Me) | H | OH |
| 7 | '' | '' | M = NOMe (syn to OMe) | '' | '' |
| 8 | '' | '' | M = NO(CH$_2$)$_3$CH$_3$ | '' | '' |
| 9 | '' | '' | M = NO(CH$_2$)O(CH$_2$)$_2$OCH$_3$ | '' | '' |
| 10 | '' | (c) | M$^1$ = H, M$^2$ = OMe | Ac | OAc |
| 11 | '' | '' | '' | H | OH |
| 12 | '' | '' | M$^1$, M$^2$ = OMe | Ac | OAc |
| 13 | '' | '' | '' | H | OH |

TABLE I-continued

Illustrative Formula 1 Derivatives

| Compound No. | R | R¹ Group | Substituents | R² | R³ |
|---|---|---|---|---|---|
| 14 | " | " | $M^1$ = OSO₂Me, $M^2$ = OMe | Ac | OAc |
| 15 | " | " | $M^1$ = OSO₂Me, $M^2$ = OMe | H | OH |
| 16 | " | " | $M^1$ = OSO₂Bn, $M^2$ = OMe | Ac | OAc |
| 17 | " | " | " | H | OH |
| 18 | CH₂OPh | (c) | $M^1$ = I, $M^2$ = OMe | Ac | OAc |
| 19 | " | " | " | H | OH |
| 20 | " | " | $M^1$ = NH₂, $M^2$ = OMe | Ac | OAc |
| 21 | " | " | " | H | OH |
| 22 | " | " | $M^1$ = pyridinium, $M^2$ = OMe | Ac | OAc |
| 23 | " | " | " | H | OH |
| 24 | " | " | $M^1$ = azido, $M^2$ = OMe | Ac | OAc |
| 25 | " | " | " | H | OH |
| 26 | " | " | $M^1$ = NH(CH₂CN), $M^2$ = OMe | Ac | OAc |
| 27 | " | " | " | H | OH |
| 28 | " | " | $M^1$ = NMe(CH₂CN), $M^2$ = OMe | Ac | OAc |
| 29 | " | " | " | H | OH |
| 30 | " | " | $M^1$ = NHMe, $M^2$ = OMe | Ac | OAc |
| 31 | " | " | " | H | OH |
| 32 | " | " | $M^1$ = NMe₂, $M^2$ = OMe | Ac | OAc |
| 33 | " | " | " | H | OH |
| 34 | " | " | $M^1$ = NH(iPr), $M^2$ = OMe | Ac | OAc |
| 35 | " | " | " | H | OH |
| 36 | CH₂OPh | (c) | $M^1$ = NHAc, $Me^2$ = OMe | Ac | OAc |
| 37 | " | " | " | H | OH |
| 38 | " | " | $M^1$ = NHPr, $M^2$ = OMe | " | " |
| 39 | " | " | $M^1$ = OTf, $M^2$ = OH | Ac | OAc |
| 40 | " | " | $M^1$ = OTf, $M^2$ = OMe | " | " |
| 41 | " | " | $M^1$ = piperidinyl, $M^2$ = OMe | " | " |
| 42 | " | " | " | H | OH |
| 43 | " | " | $M^1$ = OEtOMe, $M^2$ = OMe | Ac | OAc |
| 44 | " | " | " | H | OH |
| 45 | " | " | $M^1$ = pyrrolyl, $M^2$ = OMe | Ac | OAc |
| 46 | " | " | " | H | OH |
| 47 | " | " | $M^1$ = NHBn, $M^2$ = OMe | " | " |
| 48 | " | " | $M^1$ = NPr₂, $M^2$ = OMe | " | " |
| 49 | " | " | $M^1$ = OMe, $M^2$ = OH | Ac | OAc |
| 50 | " | " | " | H | OH |
| 51 | " | (b) | — | Ac | OAc |
| 52 | " | " | — | H | OH |
| 53 | " | (d) | — | Ac | OAc |
| 54 | ·CH₂OPh | (d) | — | H | OH |
| 55 | CH₃ | (c) | $M^1$, $M^2$ = OMe | " | " |
| 56 | " | (a) | M = O | " | " |
| 57 | " | (c) | $M^1$ = NH(iPr), $M^2$ = OMe | " | " |
| 58 | CH₂Cl | " | $M^1$, $M^2$ = OMe | " | " |
| 59 | CH₂[(3,5-diMe)-piperidin-1-yl] | " | " | " | " |
| 60 | CH₂[(3,5-diMe)-piperidin-1-yl] | " | $M^1$ = H, $M^2$ = OMe | " | " |
| 61 | CH₂OPh | " | $M^1$ = H, $M^2$ = OH | Ac | OAc |
| 62 | " | " | " | H | OH |
| 63 | " | " | $M^1$ = imidazolyl-thiocarbonyloxy, $M^2$ = OMe | Ac | OAc |
| 64 | " | " | $M^1$ = imidazolyl-thiocarbonyloxy, $M^2$ = OMe | H | OH |

The derivatives of this invention inhibit the growth of pathogenic bacteria, especially Gram-positive bacteria and Mycoplasma species and Gram-negative bacteria such as Pasteurella species. The derivatives have unexpectedly useful in vivo activity. Particularly unexpected is the ability of these derivatives to treat infections successfully when administered orally.

The minimal inhibitory concentrations (MIC's) at which illustrative compounds inhibit certain bacteria are given in Tables II and III. The MIC's in Table II were determined by standard agar-dilution assays. The MIC's in Table III were obtained using conventional broth-dilution microtiter tests.

TABLE II

Antibiotic Activity of Formula I Compounds[a]

| Test Organism | Test Compound[b] | | | | | | | | |
|---|---|---|---|---|---|---|---|---|---|
| | 2 | 4 | 6 | 7 | 10 | 11 | 13 | 15 | 17 |
| Staphylococcus aureus X1.1[c] | 0.5 | 0.5 | 2 | 1 | 0.25 | 0.25 | 2 | 2 | 4 |
| Staphylococcus aureus V41[c] | 0.5 | 1 | 2 | 1 | 0.5 | 0.25 | 2 | 2 | 4 |
| Staphylococcus aureus X400[d] | 0.5 | 1 | 2 | 1 | 0.5 | 0.25 | 2 | 2 | 4 |

TABLE II-continued

Antibiotic Activity of Formula I Compounds[a]

| Test Organism | | | | | | | | | | |
|---|---|---|---|---|---|---|---|---|---|---|
| Staphylococcus aureus S13E | 0.5 | 1 | 2 | 1 | 0.5 | 0.25 | 2 | 2 | 4 | |
| Staphylococcus epidermidis EPI1 | 1 | 1 | 2 | 1 | 0.25 | 0.25 | 2 | 2 | 4 | |
| Staphylococcus epidermidis 222 | 0.25 | 0.5 | 2 | 1 | 0.25 | 0.125 | 1 | 1 | 2 | |
| Streptococcus pyogenes C203 | 2 | 2 | 4 | 2 | 0.5 | 0.25 | 4 | 4 | 4 | |
| Streptococcus pneumoniae Park I | 4 | 2 | 1 | 0.5 | 0.5 | 0.25 | 4 | 8 | 2 | |
| Streptococcus Group D X66 | 4 | 2 | 4 | 2 | 2 | 2 | 16 | 16 | 32 | |
| Streptococcus Group D 2041 | 8 | 4 | 8 | 4 | 4 | 4 | 16 | 32 | 128 | |
| Haemophilus influenzae C.L.[e] | 64 | — | — | — | 64 | 32 | 64 | 128 | — | |
| Haemophilus influenzae 76[f] | 64 | — | — | — | 64 | 32 | 64 | 128 | — | |
| Escherichia coli EC14 | —[g] | — | — | — | — | — | — | — | — | |
| Klebsiella pneumoniae X68 | — | — | — | — | — | — | — | — | — | |
| Pseudomonas aeruginosa X239 | — | — | — | — | — | — | — | — | — | |

| Test Organism | Test Compound[b] | | | | | | | | | |
|---|---|---|---|---|---|---|---|---|---|---|
| | 19 | 20 | 21 | 22 | 25 | 27 | 29 | 31 | 33 | 35 |
| Staphylococcus aureus X1.1 | 8 | 0.25 | 0.25 | 2 | 4 | 0.5 | 2 | 0.5 | 4 | 8 |
| Staphylococcus aureus V41[c] | 8 | 0.25 | 0.5 | 4 | 4 | 1 | 2 | 0.5 | 4 | 16 |
| Staphylococcus aureus X400[d] | 8 | 0.5 | 0.25 | 4 | 4 | 0.5 | 2 | 0.5 | 2 | 16 |
| Staphylococcus aureus S13E | 8 | 0.5 | 0.25 | 4 | 4 | 0.5 | 2 | 0.25 | 4 | 16 |
| Staphylococcus epidermidis EPI1 | 8 | 0.5 | 0.5 | 2 | 4 | 0.5 | 1 | NT | 2 | 8 |
| Staphylococcus epidermidis 222 | 8 | 0.25 | 0.25 | 4 | 4 | 0.5 | 2 | 0.5 | 2 | 8 |
| Streptococcus pyogenes C203 | 8 | 0.25 | 0.5 | 4 | 8 | NT[h] | NT | 0.125 | NT | NT |
| Streptococcus pneumoniae Park I | 8 | 1 | 1 | 2 | 8 | NT | NT | 0.125 | NT | NT |
| Streptococcus Group D X66 | 8 | 4 | 4 | 16 | 16 | 8 | 32 | 2 | 32 | 64 |
| Streptococcus Group D 2041 | 8 | 8 | 8 | 16 | 64 | 16 | 64 | 2 | 64 | 128 |
| Haemophilus influenzae C.L.[e] | — | 16 | 32 | 64 | — | 4 | 16 | 32 | 64 | 128 |
| Haemophilus influenzae 76[f] | — | 16 | 16 | 32 | — | 8 | 32 | NT | 64 | 128 |
| Escherichia coli EC14 | — | — | — | — | — | — | — | — | — | — |
| Klebsiella pneumoniae X68 | — | — | — | — | — | — | — | — | — | — |
| Pseudomonas aeruginosa X239 | — | — | — | — | — | — | — | — | — | — |

| Test Organism | Test Compound[b] | | | | | | | | | |
|---|---|---|---|---|---|---|---|---|---|---|
| | 37 | 38 | 40 | 42 | 44 | 46 | 47 | 48 | 50 | 52 | 54 |
| Staphylococcus aureus X1.1 | 8 | 16 | 2 | 4 | 2 | 8 | 2 | 16 | 0.5 | 0.5 | 1 |
| Staphylococcus aureus V41[c] | 4 | 16 | 2 | 4 | 2 | 8 | 2 | 16 | 0.5 | 0.5 | 1 |
| Staphylococcus aureus X400[d] | 4 | 16 | 2 | 4 | 2 | 8 | 2 | 16 | 0.5 | 0.5 | 0.5 |
| Staphylococcus aureus S13E | 4 | 8 | 2 | 2 | 2 | 8 | 2 | 16 | 0.5 | 0.5 | 1 |
| Staphylococcus epidermidis EPI1 | 8 | 16 | 2 | 4 | 2 | 8 | 2 | 16 | 0.5 | 0.5 | 1 |
| Staphylococcus epidermidis 222 | 8 | 8 | 2 | 2 | 2 | 4 | 2 | 16 | 0.25 | 0.25 | 0.25 |
| Streptococcus pyogenes C203 | 2 | 4 | 2 | 2 | 4 | 16 | 2 | 8 | 4 | 1 | 4 |
| Streptococcus pneumoniae Park I | 4 | NT | 8 | 2 | 4 | 2 | 2 | 4 | 8 | 2 | 4 |
| Streptococcus Group D X66 | 64 | 16 | — | 16 | 8 | 32 | 8 | 16 | 16 | 2 | 8 |
| Streptococcus Group D 2041 | 128 | 64 | — | 32 | 32 | 64 | 32 | 16 | 32 | 2 | 8 |
| Haemophilus influenzae C.L.[e] | — | — | — | — | — | — | 128 | — | 128 | 64 | 128 |
| Haemophilus influenzae 76[f] | — | — | — | — | — | — | 128 | — | NT | 64 | 128 |
| Escherichia coli EC14 | — | — | — | — | — | — | — | — | — | — | — |
| Klebsiella pneumoniae X68 | — | — | — | — | — | NT | — | — | — | — | — |
| Pseudomonas aeruginosa X239 | — | — | — | — | — | — | — | — | — | — | — |

[a]MIC in mcg/mL;
[b]Compound numbers from Table I;
[c]Penicillin-resistant strain;
[d]Methicillin-resistant strain;
[e]Ampicillin-sensitive strain;
[f]Ampicillin-resistant strain;
[g]Not active at 128 mcg/mL, the highest level tested;
[h]not tested

TABLE III

Antibiotic Activity of Formula 1 Compounds[a]

| Test Organism | Test Compound[b] | | | | |
|---|---|---|---|---|---|
| | 4 | 10 | 11 | 13 | 21 |
| Staphylococcus aureus | 1.56 | 0.78 | 0.78 | 3.12 | 0.39 |
| Streptococcus sp. 19F | 0.78 | 6.25 | 12.5 | 6.25 | 3.12 |
| Pasteurella multocida 17E[c] | 50 | 50 | 25 | — | 25 |
| Pasteurella multocida 60A[d] | —[e] | — | 25 | — | 12.5 |
| Pasteurella multocida 40G | 50 | — | 25 | 50 | 6.25 |
| Pasteurella multocida 22A | — | — | 25 | — | 12.5 |
| Pasteurella multocida 68C | 50 | 50 | 12.5 | 50 | 12.5 |
| Pasteurella hemolytica 23C | — | 50 | 25 | — | 25 |
| Pasteurella hemolytica 41D | — | 50 | 25 | — | 12.5 |
| Pasteurella hemolytica 22C | — | — | 25 | — | 25 |
| Bordetella bronchiseptica | — | — | — | — | — |
| Mycoplasma gallisepticum 29C | 1.56 | <0.048 | 0.39 | 1.56 | 1.56 |
| Mycoplasma gallisepticum 15E | 25 | NT | 12.5 | — | — |
| Mycoplasma gallisepticum 36H | 50 | 25 | 25 | — | — |
| Mycoplasma synoviae 40A | NT[f] | 3.12 | 1.56 | 6.25 | NT |
| Mycoplasma hyorhinis 29E | NT | 25 | 25 | 25 | NT |
| Mycoplasma hyopneumoniae | — | 6.25 | >25 | >25 | 50 |
| S5972 | | | | | |

[a]MIC in mcg/mL
[b]Compound numbers from Table I
[c]Bovine isolate
[d]Avian isolate
[e]not active at 50 mcg/mL
[f]not tested The formula 1 compounds have shown in vivo antimicrobial activity against experimentally-induced infections in laboratory animals. When two doses of test compound were administered to mice experimentally infected with *Streptococcus pyogenes* C203, the activity observed was measured as an $ED_{50}$ value [effective dose in mg/kg to protect 50% of the test animals: see Warren Wick, et al., *J. Bacteriol.* 81, 233–235 (1961)]. ED$_{50}$ values observed for illustrative compounds are given in Table IV.

TABLE IV

ED$_{50}$ Values of Formula 1 Compounds vs. *Streptococcus pyogenes* C203 in Mice[a]

| Test Compound[b] | Subcutaneous | Oral |
|---|---|---|
| 2 | >10 | 85.6 |
| 4 | >10 | 39.6 |
| 11 | 10 | 34 |
| 13 | >10, >10[c] | 18.8, 22.4 |
| 15 | >10 | 29.3 |
| 21 | >10 | 57.4 |
| 25 | >10 | 64 |
| 42 | >10 | >100 |
| 47 | >10 | 70.7 |
| 50 | >10 | 75.3 |
| 52 | 10 | 79.4 |

[a] mg/kg × 2; doses given 1 and 4 hours post-infection
[b] Compound numbers from Table I.
[c] Results of two tests This invention also relates to methods of controlling infections caused by bacterial and mycoplasmal species. In carrying out the methods of this invention, an effective amount of a formula 1 compound is administered parenterally or orally to an infected or susceptible warm-blooded animal.

The dose which is effective to control the infection will vary with the severity of the infection and the age, weight, and condition of the animal. The total dose required for protection parenterally will generally, however, be in the range of from about 0.1 to about 100 mg/kg and preferably will be in the range of from about 0.1 to about 30 mg/kg. The dose required for oral administration will generally be in the range of from about 1 to about 300 mg/kg and preferably will be in the range of from about 1 to about 100 mg/kg. Suitable dosage regimens can be constructed.

Often the most practical way to administer the compounds is by formulation into the feed supply or drinking water. A variety of feeds, including the common dry feeds, liquid feeds, and pelleted feeds, may be used.

In another aspect, this invention relates to compositions useful for the control of infections caused by bacteria and Mycoplasma species. These compositions comprise a formula 1 compound together with a suitable vehicle. Compositions may be formulated for parenteral or oral administration by methods recognized in the pharmaceutical art.

The methods of formulating drugs into animal feeds are well-known. A preferred method is to make a concentrated-drug premix which in turn is used to prepare medicated feeds. Typical premixes may contain from about 1 to about 200 grams of drug per pound of premix. Premixes may be either liquid or solid preparations.

The final formulation of feeds for animals or poultry will depend upon the amount of drug to be administered. The common methods of formulating, mixing, and pelleting feeds may be used to prepare feeds containing a formula 1 compound.

Effective injectable compositions containing these compounds may be in either suspension or solution form. In the preparation of suitable formulations it will be recognized that, in general, the water solubility of the acid addition salts is greater than that of the free bases. Similarly, the bases are more soluble in dilute acids or in acidic solutions than in neutral or basic solutions.

In the solution form the compound is dissolved in a physiologically acceptable vehicle. Such vehicles comprise a suitable solvent, preservatives such as benzyl alcohol, if needed, and buffers. Useful solvents include, for example, water and aqueous alcohols, glycols, and carbonate esters such as diethyl carbonate.

Injectable suspension compositions require a liquid suspending medium, with or without adjuvants, as a vehicle. The suspending medium can be, for example, aqueous polyvinylpyrrolidone, inert oils such as vegetable table oils or highly refined mineral oils, or aqueous carboxymethylcellulose.

Suitable physiologically acceptable adjuvants are necessary to keep the compound suspended in suspension compositions. The adjuvants may be chosen from among thickeners such as carboxymethylcellulose, polyvinylpyrrolidone, gelatin and the alginates. Many surfactants are also useful as suspending agents. Lecithin, alkylphenol polyethylene oxide adducts, naphthalenesulfonates, alkylbenzenesulfonates, and the polyoxyethylene sorbitan esters are useful suspending agents.

Many substances which affect the hydrophilicity, density, and surface tension of the liquid suspending medium can assist in making injectable suspensions in individual cases. For example, silicone antifoams, sorbitol, and sugars can be useful suspending agents.

In order to illustrate more fully the operation of this invention, the following examples are provided. In these examples the abbreviation "20-DH" is used for the term "20-dihydro", Ac means acetyl and Ph means phenyl.

PREPARATION 1

A. Purification of cis-3,5-Dimethylpiperidine

A solution containing 3,5-dimethylpiperidine (40 mL, a 4:1 mixture of cis:trans isomers), triethylamine (42 mL) and dichloromethane (250 mL) was stirred while o-chlorobenzoyl chloride (38.2 mL) was added dropwise at a rate sufficient to maintain gentle reflux. At the completion of the addition, the solution was stirred for another half hour; then ten percent aqueous ammonium chloride solution (200 mL) and sufficient conc. HCl to make the aqueous layer acidic were added. The organic layer was separated, washed with brine, dried and concentrated. The solid obtained was recrystallized twice from CH$_2$Cl$_2$ and hexane to give essentially pure cis-amide, mp 99°–103° C.

The amide (17 g) was dissolved in ethylene glycol. Potassium hydroxide pellets (11 g) were added, and the solution was heated to reflux. After one hour, the flask was arranged for downward distillation, and the fraction boiling between 100° C. and 195° C. was collected. This material was partitioned between water and ether, dried and concentrated to afford pure cis-3,5-dimethylpiperidine.

B. Alternate Purification of cis-3,5-Dimethylpiperidine

A 1-liter, 3-neck flask was charged with 48 mL (0.36 mol) of commercial grade 3,5-dimethylpiperidine (ca. 80–85% cis) and 600 mL of anhydrous ether. HCl gas was bubbled through the solution with vigorous stirring until no free amine remained. The product which formed was separated by filtration and air-dried to give 47 g of the hydrochloride salt, mp 160°–180° C.

The salt was suspended in acetone (600 mL) and heated to reflux for 1 hr. The reaction mixture was cooled to 50° C. and filtered; the separated solid was air-dried to yield 25.6 g of product, mp 226°–228° C. A portion of this material (18 g) was dissolved in water (100 mL), and the solution was adjusted to pH 10 with sodium hydroxide pellets. The free amine was extracted into diethyl ether, dried over magnesium sulfate, filtered and carefully concentrated to yield 8.5 mL of cis-3,5-dimethylpiperidine, contaminated with ≦5% of the trans isomer.

C. Preparation of cis-20-DH-20-Deoxy-20-(3,5-dimethylpiperidin-1-yl)desmycosin Desmycosin (10 g, 12.9 mmol) was dissolved in dry methanol (100 mL), and cis-3,5-dimethylpiperidine (4 g, 35 mmol) was added. After the mixture was stirred for 30 minutes at room temperature, sodium cyanoborohydride (0.8 g, 12.9 mmol) was added. The solution was stirred overnight and then was evaporated under reduced pressure. The residue was partitioned between ethyl acetate and water (150 mL each). The organic layer was then extracted sequentially with pH 6.5 phosphate buffer (100 mL) and pH 4.5 phosphate buffer (100 mL).

The latter solution was adjusted to pH 10 with 5N sodium hydroxide, and the free amine was reextracted into ethyl acetate. The solution was dried over magnesium sulfate, filtered and concentrated to yield 6.0 g of 20-DH-20-deoxy-20-(cis-3,5-dimethylpiperidine-1-yl)desmycosin. Analysis of the product by reverse-phase HPLC detected no trans-isomer.

PREPARATION 2

Separation of cis- and trans-20-DH-20-Deoxy-20-(3,5-dimethylpiperidin-1-yl)desmycosin 20-DH-20-Deoxy-20-(3,5-dimethylpiperidin-1-yl)desmycosin was prepared using 3,5-dimethylpiperidine which was a mixture of cis:trans-isomers (4:1). The product was chromatographed over silica gel using a methanol:dichloromethane:ammonium hydroxide (49.5:49.5:1) solvent system. A single major peak was eluted. The first ten percent of this peak consisted of pure cis-isomer, and the last ten percent consisted of enriched trans-isomer (cis:trans material in a ratio of 16:84).

EXAMPLE 1

2',4'-Di-O-acetyl-4''-oxo-20-DH-20-O-phenyl-desmycosin (Compound 1)

A suspension of N-chlorosuccinimide (1.35 g, 1.1 eq.) in $CH_2Cl_2$ (65 mL) under argon in a dry ice/acetone bath was treated with diisopropyl sulfide (1.90 mL, 1.2 eq.). After 30 minutes, the resulting solution was added to a cooled solution (dry ice/acetone) of 2',4'-di-O-Ac-20-DH-O-Ph-desmycosin (10.0 g, 10.7 mmol) in $CH_2Cl_2$ (50 mL). Two hours later, triethylamine (1.65 mL, 1.1 eq.) was added, and the cold solution was allowed to warm slowly to room temperature. The solution was then shaken with water (250 mL), and the aqueous phase was separated and extracted with $CH_2Cl_2$ (2×50 mL). The organic layers were combined, dried ($Na_2SO_4$) and evaporated to dryness. The residue was chromatographed on a Waters Prep 500 LC silica-gel column, using an 8-L gradient of hexane→ethyl acetate/hexane (3:1) as the eluent, to give 3.45 g (34.6%) of the title compound as a white solid foam.

UV (EtOH): $\lambda_{max}$ 279 nm ($\epsilon$ 23,835)
IR ($CHCl_3$): 1746, 1678, 1595 cm$^{-1}$
$^1$H NMR ($CDCl_3$): δ 4.92 (dd, 2'-H), 4.75 (dd, 4'-H), 4.18 (q, 5''-H), 3.70 (d, 3''-H), 2.05 (s, 3H), 2.02 (s, 3H).
MS(FD): m/e 931 (M).

EXAMPLE 2

4''-Oxo-20-DH-20-O-phenyl-desmycosin (Compound 2)

A solution of 2',4'-di-O-Ac-4''-oxo-20-DH-20-O-Ph-desmycosin (391 mg, 0.42 mmol) in MeOH (5 mL) was allowed to stand at room temperature for 4 days. The solution was evaporated to dryness. The residue was chromatographed (Chromatotron), using EtOAc/MeOH (4:1) as the eluent, to give 209 mg (58.8%) of the title compound.

UV (EtOH): $\lambda_{max}$ 277 nm ($\epsilon$ 21,350)
IR ($CHCl_3$): 1729(sh), 1714, 1677, 1596 cm$^{-1}$
$^1$H NMR ($CDCl_3$): δ 4.19 (q, 5''-H)
MS(FD): m/e 848 (M+H).

EXAMPLE 3

4''-O-Hydroxyimino-20-DH-20-O-phenyl-desmycosin (Compound 4)

2',4'-Di-O-Ac-4''-oxo-20-DH-20-O-Ph-desmycosin (1.0 g, 1.07 mmol) was treated with a solution of hydroxylamine hydrochloride (112 mg, 1.5 eq.) and 1N sodium hydroxide (1.6 mL) in ethanol (10 mL). After 7 days at room temperature, the reaction solution was diluted with saturated $NaHCO_3$ solution (100 mL) and extracted with $CH_2Cl_2$ (3×50 mL). The organic extracts were dried ($Na_2SO_4$) and evaporated to dryness. The residue was chromatographed on a silica-gel flash column, using a 1-L gradient of $CH_2Cl_2$→$CH_2Cl_2$/MeOH/conc. $NH_4OH$ (90:10:0.5) followed by 500 mL of $CH_2Cl_2$/MeOH/conc. $NH_4OH$ (90:10:0.5) as the eluent, to give 307 mg (33.2%) of the title compound as a white solid foam.

UV (EtOH): $\lambda_{max}$ 279 nm ($\epsilon$ 23,251)
IR ($CHCl_3$): 3590, 1713, 1675, 1595 cm$^{-1}$
$^1$H NMR ($CDCl_3$): δ 5.14 (d, 3''-H), 4.38 (q, 5''-H)
MS(FD): m/e 863 (M+H).

EXAMPLE 4

4''-O-Methoxyimino-20-DH-20-O-phenyl-desmycosin (Compounds 6 and 7)

A solution of 2',4'-di-O-Ac-4''-oxo-20-DH-20-O-Ph-desmycosin (2.00 g, 2.15 mmol) in MeOH (50 mL) was cooled in an ice/water bath; then methoxylamine hydrochloride (359 mg, 2 eq.) and sodium acetate (705 mg, 4 eq.) were added. The colorless solution was allowed to warm slowly to room temperature overnight. The solution was concentrated in vacuo to a volume of ~10 mL and then was diluted with saturated $NaHCO_3$ solution (200 mL). This mixture was extracted with $CH_2Cl_2$ (3×50 mL), dried ($Na_2SO_4$) and evaporated to dryness. The residual foam was chromatographed on a silica-gel flash column, using a 1-L gradient of $CH_2Cl_2$→$CH_2Cl_2$/MeOH (9:1) followed by 1 L of $CH_2Cl_2$/MeOH (9:1) as the eluent, to give 1.20 g (63.8%) of the title compound as a solid foam.

The isomers were separated by preparative reverse-phase HPLC, using an 8-L gradient of 0.2M $NaClO_4$/$CH_3CN$ (4:1)→0.2M $NaClO_4$/$CH_3CN$ (2:3) followed by 2 L of 0.2M $NaClO_4$/$CH_3CN$ (2:3) as the eluent, to give 677 mg of the major isomer (Compound 7) as a white solid foam:

UV (EtOH): $\lambda_{max}$ 279 nm ($\epsilon$ 24,017)
IR (CHCl$_3$): 1714, 1679, 1594 cm$^{-1}$
$^1$H NMR (CDCl$_3$): δ 5.00 (d, 3"-H), 4.76 (d, 1"-H), 4.30 (q, 5"-H), 3.29 (s, N-OMe), 2.97 (dd, 2"-H)
MS(FD): m/e 877 (M+H).

The minor isomer (Compound 6) was obtained as a mixture containing 20% of the major isomer:
$^1$H NMR (CDCl$_3$): δ 4.88 (q, 5"-H), 4.72 (d, 1"-H), 4.12 (d, 3"-H), 3.56 (overlapped with 2"-H).

EXAMPLE 5

2',4'-Di-O-acetyl-4"-O-[(imidazol-1-yl)thiocarbonyl]-20-DH-20-O-phenyl-desmycosin (Compound 63)

A solution of 2',4'-di-O-Ac-20-DH-20-O-Ph-desmycosin (933 mg, 1.0 mmol) in THF (12 mL) under argon was treated with 1,1'-thiocarbonyldiimidazole (210 mg, 1.2 eq.). After 1 hr., the reaction mixture was evaporated to dryness. The residue was taken up in toluene, filtered and evaporated to give a glass. The residue was chromatographed on a silica-gel flash column, using a 1200-mL gradient of toluene→ethyl acetate/toluene (2:1) followed by 600 mL of ethyl acetate/toluene (2:1) as the eluent, to give 920 mg of the title compound as a colorless glass.
UV (EtOH): $\lambda_{max}$ 278 nm ($\epsilon$ 30,850)
IR (CHCl$_3$): 1744, 1585 cm$^{-1}$
$^1$H NMR (CDCl$_3$): δ 8.36 (dd, 1-H), 7.64 (dd, 1H), 5.15 (dd, 4"-H)
MS(FD): m/e 1043 (M+H).

EXAMPLE 6

2',4'-Di-O-acetyl-4"-deoxy-20-DH-20-O-phenyl-desmycosin (Compound 10)

A solution of 2',4'-di-O-Ac-4"-O-[(imidazol-1-yl)thiocarbonyl-20-DH-20-O-Ph-desmycosin (3.03 g, 2.91 mmol) in degassed toluene (60 mL) under an argon atmosphere was treated with tri(n-butyl)tin hydride (0.95 mL) and a few milligrams of 2,2'-azobisisobutyronitrile (AIBN). The solution was heated at reflux for 26 hrs., periodically adding AIBN and adding tri(n-butyl)tin hydride (0.23 mL) after 3 hrs. The reaction solution was evaporated to give a glass, and the residue was partitioned between hexanes and acetonitrile. The acetonitrile layer was removed, washed with hexanes (2×) and evaporated to dryness. The residue obtained was chromatographed on a Waters Prep 500 LC (silica-gel column), using an 8-L gradient of toluene→ethyl acetate/toluene (2:1) followed by 1.5 L of ethyl acetate/toluene (2:1) as the eluent, to give the title compound.
UV (EtOH): $\lambda_{max}$ 278 nm ($\epsilon$ 21,250)
IR (CHCl$_3$): 1751, 1711, 1682, 1599 cm$^{-1}$
MS(FD): m/e 917 (M).

EXAMPLE 7

4"-Deoxy-20-DH-20-O-phenyl-desmycosin (Compound 11)

A solution of 2',4'-di-O-Ac-4"-deoxy-20-DH-20-O-Ph-desmycosin (285 mg, 0.31 mmol) in methanol (5 mL) was heated at 45° C. for 18 hrs. The solution was evaporated to dryness to give 235 mg (91%) of the title compound as a glass.
UV (EtOH): $\lambda_{max}$ 278 nm ($\epsilon$ 19,880)
IR (CHCl$_3$): 1712, 1678, 1599 cm$^{-1}$
MS(FD): m/e 833 (M).

EXAMPLE 8

2',4'-Di-O-acetyl-20-DH-20-O-phenyl-4"-O-(trifluoromethanesulfonyl)-desmycosin (Compound 40)

A solution of 2',4'-di-O-Ac-20-DH-20-O-Ph-desmycosin (10.0 g, 10.7 mmol) in CH$_2$Cl$_2$ (45 mL) at 0° C. was treated successively with pyridine (5.0 mL) and trifluoromethanesulfonic anhydride (2.25 mL, 1.25 eq). The solution was kept at 0° C. for 2 hrs. with the exclusion of moisture; then ice/water (50 g) was added. Saturated NaHCO$_4$ solution (250 mL) was added to this mixture. The product was extracted with CH$_2$Cl$_2$ (3×50 mL), dried (Na$_2$SO$_4$) and evaporated to dryness to give a solid foam.

The product was chromatographed on a Waters Prep 500 LC (silica-gel column), using an 8-L gradient of toluene→toluene/ethyl acetate (4:1) followed by 2 L of toluene/ethyl acetate (4:1) and 2 L of toluene/ethyl acetate (3:1) as the eluent, to give 5.90 g (51.7%) of the title compound as a white solid foam.
UV (EtOH): $\lambda_{max}$ 279 nm ($\epsilon$ 23,529)
IR (CHCl$_3$): 1744, 1715(sh), 1679, 1595 cm$^{-1}$
$^1$H NMR (CDCl$_3$): δ 4.92 (dd, 2'-H, overlap with 15-H), 4.76 (dd, 4'-H), 4.39 (m, 4"-H, overlap with 1"-H)
MS(FD): m/e 1065 (M).

EXAMPLE 9

4"-O-Methyl-20-DH-20-O-phenyl-desmycosin (Compound 13)

A solution of 2',4'-di-O-Ac-20-DH-20-O-Ph-4"-O-(trifluoromethanesulfonyl)-desmycosin (1.0 g, 0.94 mmol) in MeOH (10 mL) was allowed to stand for 48 hrs. at room temperature with the exclusion of moisture. The solution was diluted with CH$_2$Cl$_2$ (50 mL), washed with saturated NaHCO$_4$ solution (50 mL), dried (Na$_2$SO$_4$) and evaporated to dryness to give the title compound as a pale-yellow solid foam.
UV (EtOH): $\lambda_{max}$ 277 nm ($\epsilon$ 21,900)
IR (CHCl$_3$): 1715, 1676, 1593 cm$^{-1}$
$^1$H NMR (CDCl$_3$): δ 3.81 (dd, 4"-H)
MS(FD): m/e B64 (M+H).

EXAMPLE 10

2',4'-Di-O-acetyl-20-DH-20-O-phenyl-4"-O-(trifluoromethanesulfonyl)-lactenocin (Compound 39)

2',4'-Di-O-Ac-20-DH-20-O-Ph-lactenocin (7.5 g, 8.16 mmol) was treated as described in Example 8. The crude product was chromatographed on a silica-gel flash column, using ethyl acetate/hexane (3:1) as the eluent, to give 3.15 g (36.7%) of the title compound as a pale-yellow solid foam.
UV (EtOH): $\lambda_{max}$ 279 nm ($\epsilon$ 22,510)
IR (CHCl$_2$): 1745, 1709(sh), 1670, 1595 cm$^{-1}$
$^1$H NMR (CDCl$_3$): δ 4.94 (dd, 2'-H, overlap with 15-H), 4.80 (dd, 4'-H), 4.41 (dd, 4"-H, overlap with 1'-H)
MS(FD): m/e 1051 (M).

EXAMPLES 11 AND 12

4"-O-Methyl-20-DH-20-O-phenyl-lactenocin (Compound 50) and
4"-Deoxy-3"-oxo-20-DH-20-O-phenyl-lactenocin (Compound 52)

A solution of 2',4'-di-O-Ac-20-DH-20-O-Ph-4"-O-(trifluoromethanesulfonyl)-lactenocin (1.60 g, 1.5 mmol) in MeOH (20 mL) was allowed to stand at room temperature for 3 days. The solution was evaporated to dryness to give a glass. The residue was dissolved in $CH_2Cl_2$ (100 mL), extracted with saturated $NaHCO_4$ solution (3×50 mL), dried ($Na_2SO_4$) and evaporated to give a residue. The residue was chromatographed on a silica-gel flash column, using a 1-L gradient of $CH_2Cl_2 \rightarrow CH_2Cl_2/MeOH$ (9:1) followed by 500 mL of $CH_2Cl_2/MeOH$ (9:1) as the eluent, to give the title compounds.

4″-Deoxy-3″-oxo-20-DH-20-O-Ph-lactenocin:

UV (EtOH) $\lambda_{max}$ 279 nm ($\epsilon$ 21,320)
IR ($CHCl_3$): 1728, 1715, 1678, 1594 $cm^{-1}$
$^1$H NMR ($CDCl_3$): δ 3.64 (dd, 2″-H), 2.42 (m, 4″-H)
MS(FD): m/e 818 (M+H).

4″-OMe-20-DH-20-O-Ph-laotenocin:

UV (EtOH): $\lambda_{max}$ 279 nm ($\epsilon$ 23,332)
IR ($CHCl_3$): 1713, 1678, 1594 $cm^{-1}$
$^1$H NMR ($CDCl_3$): δ 3.54 (s, $OCH_3$), 3.44 (s, $OCH_3$), 2.85 (dd, 4″-H)
MS(FD): m/e 850 (M+H).

EXAMPLE 13

2′,4′-Di-O-acetyl-3″,4″-anhydro-20-DH-20-O-phenyl-desmycosin (Compound 53)

A solution of 2′,4′-di-O-Ac-20-DH-20-O-Ph-4″-O-(trifluoromethanesulfonyl)-desmycosin (1.70 g, 1.6 mmol) and 1,8-diazabicyclo[5.4.0]-undec-7-ene (DBU) (0.48 mL, 2 eq.) in THF (50 mL) was heated at 50° C. for 24 hr with the exclusion of moisture. The solution was concentrated in vacuo and diluted with $CH_2Cl_2$ (150 mL). The $CH_2Cl_2$ solution was washed with a saturated $NaHCO_3$ solution (2×50 mL), dried ($Na_2SO_4$) and evaporated to dryness. The residue was chromatographed on a Chromatotron (silica-gel, 4-mm rotor), using ethyl acetate/hexane (3:1) as the eluent, to give 889 mg (60.9%) of the title compound.

UV (EtOH): $\lambda_{max}$ 279 nm ($\epsilon$23,560)
IR ($CHCl_3$) 1744, 1720(sh), 1682, 1595 $cm^{-1}$
$^1$H NMR ($CDCl_3$) δ4.67 (bs, 4″-H), 4.39 m, 5″-H, overlap with 1′-H)
MS(FD): m/e 915 (M).

EXAMPLE 14

3″,4″-Anhydro-20-DH-20-O-phenyl-desmycosin (Compound 54)

A solution of 2′,4′-di-O-Ac-3″,4″-anhydro-20-DH-20-O-Ph-desmycosin (828 mg, 0.90 mmol) in MeOH (10 mL) was allowed to stand at room temperature for 48 hrs. The solution was evaporated to dryness to give a white solid foam. The foam was chromatographed on a silica-gel flash column, using a 1-L gradient of $CH_2Cl_2 \rightarrow CH_2Cl_2/MeOH$ (9:1) followed by 500 mL of $CH_2Cl_2/MeOH$ (9:1) as the eluent, to give 533 mg (70.9%) of the title compound as a white solid foam.

UV (EtOH): $\lambda_{max}$ 279 nm ($\epsilon$22,669)
IR ($CHCl_3$) 1714, 1678, 1666, 1594 $cm^{-1}$
$^1$H NMR ($CDCl_3$) δ4.68 bs, 4′-H), 4.39 (dd, 5″-H)
MS(FD): m/e 831 (M).

EXAMPLE 15

2′,4′-Di-O-acetyl-441-O-methanesulfonyl-20-DH-20-O-phenyl-desmycosin (Compound 14)

A solution of 2′,4′-di-O-Ac-20-DH-20-O-Ph-desmycosin (1.0 g, 1.07 mmol) and pyridine (1.0 mL) in $CH_2Cl_2$ (9.0 mL) was cooled to 0° C. The cold solution was treated with methanesulfonyl chloride (90 μL, 1.18 mmol) and allowed to warm to room temperature with the exclusion of moisture. After 3 days, the reaction mixture was diluted with saturated $NaHCO_3$ solution (50 mL), extracted with $CH_2Cl_2$ (4×25 mL), dried ($Na_2SO_4$) and evaporated to dryness to give a white solid foam. The foam was chromatographed on a Chromatotron (silica-gel, 4-mm rotor), using ethyl acetate as the eluent, to give 968 mg (89.3%) of the title compound as a white solid foam.

UV (EtOH): $\lambda_{max}$ 277 nm ($\epsilon$21,900)
IR ($CHCl_3$) 1742, 1711(sh), 1676, 1591 $cm^{-1}$
$^1$H NMR ($CDCl_3$) 6 4.92 (dd, 2′-H, overlap with 15-H), 4.75 (dd, 4′-H), 4.22 (dd, 4″-H), 3.10 (s, $OSO_2CH_3$)
MS(FD): m/e 1011 (M).

EXAMPLE 16

4″-O-Methanesulfonyl-20-DH-20-O-Phenyl-desmycosin (Compound 15)

A solution of 2′,4′-di-O-Ac-4″-O-methanesulfonyl-20-DH-20-O-Ph-desmycosin (500 mg, 0.49 mmol) in MeOH (5 mL) was heated at reflux for 6 hr. The solution was evaporated to dryness to give the title compound as a white solid foam.

UV (EtOH): $\alpha_{max}$ 277 nm ($\epsilon$22,650)
IR ($CHCl_3$): 1708, 1647, 1614 $cm^{-1}$
$^1$H NMR ($CDCl_3$): δ4.23 (dd, 4″-H), 3.10 (s, $OSO_2CH_3$) MS(FD): m/e 928 (M+H).

EXAMPLE 17

2′,4′-Di-O-acetyl-4″-O-benzylsulfonyl-20-DH-20-O-phenyldesmycosin (Compound 16)

Using the procedure described in Example 15, 2′,4′-di-O-Ac-20-DH-20-O-Ph-desmycosin (1.0 g, 1.07 mmol) was reacted with benzylsulfonyl chloride (225 mg, 1.18 mmol). Chromatography on a Chromatotron (4-mm rotor, silica-gel), using ethyl acetate as the eluent, gave the title compound as a white solid foam.

UV (EtOH): $\lambda_{max}$ 279 nm ($\epsilon$23,342)
IR ($CHCl_3$) 1743, 1710(sh), 1667, 1594 $cm^{-1}$
$^1$H NMR ($CDCl_3$): δ4.92 (dd, 2′-H, overlap with 15-H), 4.76 (dd, 2′H), 4.42 (s, $OSO_2CH_2$-, overlap with 1′-H), 4.17 (dd, 4″-H)
MS(FD): m/e 1087 (M).

EXAMPLE 18

4″-O-Benzylsulfonyl-20-DH-20-O-phenyl-desmycosin (Compound 17)

A solution of 2′,4′-di-O-Ac-4″-O-benzylsulfonyl-20-DH-20-O-Ph-desmycosin (326 mg, 0.30 mmol) in MeOH (15 mL) was heated at reflux for 3 hr. The solution was evaporated to dryness to give the title compound as a colorless glass.

UV (EtOH): $\lambda_{max}$ 279 nm ($\epsilon$21,457)
IR ($CHCl_3$): 1707, 1689, 1594 $cm^{-1}$
$^1$H NMR ($CDCl_3$): δ4.41 (s, $OSO_2CH_2$—), 4.17 (dd, 4″-H)
MS(FD): m/e 1004 (M+H).

EXAMPLES 19-20

2',4'-Di-O-acetyl-4''-deoxy-4''-iodo-20-DH-20-O-phenyldesmycosin (Compound 18)

2',4'-Di-O-acetyl-4''-deoxy-3''-oxo-20-DH-20-O-phenyllactenocin (Compound 51)

A solution of 2',4'-di-O-Ac-20-DH-20-O-Ph-4''-O-(trifluoromethanesulfonyl)-desmycosin (5.0 g, 4.70 mmol) and NaI (3.5 g, 5 eq.) in ethylene glycol dimethyl ether (DME) (25 mL) was heated at 70° C. for 6 hr. under a nitrogen atmosphere. The reaction solution was diluted with deionized H$_2$O (150 mL) and extracted with CHCl$_3$ (3×50 mL). The combined CHCl$_3$ extracts were washed with saturated NaHCO$_3$ solution (50 mL), dried (Na$_2$SO$_4$) and evaporated to dryness. The residue was chromatographed on a silica-gel flash column, using a 1-L gradient of toluene toluene/acetone (4:1) followed by 500 mL of toluene/acetone (4:1) as the eluent, to give 1.82 g (37.2%) of 2',4'-di-O-Ac-4''-deoxy-4''-iodo-20-DH-20-O-Ph-desmycosin and 1.28 g (30.3%) of 2',4'-di-O-Ac-4''-deoxy-3''-oxo-20-DH-20-O-Ph-lacetenocin.

2',4'-Di-O-Ac-4''-deoxy-4''-iodo-20-DH-20-O-Ph-desmycosin:

UV (EtOH): $\lambda_{max}$ 279 nm ($\epsilon$23,278)
IR (CHCl$_3$) 1745, 1718(sh), 1680, 1594 cm$^{-1}$
$^1$H NMR (acetone-d$_6$) $\delta$ 4.87 (dd, 2'-H), 4.71 (dd, 4'-H), 4.02 (dd, 4''-H)
MS(FD): m/e 1043 (M).

2',4'-Di-O-Ac-4''-deoxy-3''-oxo-20-DH-20-O-Ph-lactenocin:

UV (EtOH): $\lambda_{max}$ 279 nm ($\epsilon$22,788)
IR (CHCl$_3$) 1740, 1718(sh), 1680, 1594 cm$^{-1}$
$^1$H NMR (CDCl$_3$) $\delta$ 4.93 (dd, 2'-H), 4.76 (dd, 4'-H), 3.64 (dd, 2''-H), 2.42 (m, 4''-H)
MS(FD): m/e 901 (M).

EXAMPLE 12

4''-Deoxy-4''-iodo-20-DH-20-O-phenyl-desmycosin (Compound 19)

A solution of 2',4'-di-O-Ac-4''-deoxy-4''-iodo-20-DH-20-O-Ph-desmycosin (1.71 g, 1.64 mmol) in MeOH (25 mL) was allowed to stand at room temperature for 45 hr. The solution was evaporated to dryness to give the title compound as a white solid foam.

UV (EtOH): $\lambda_{max}$ 279 nm ($\epsilon$24,307)
IR (CHCl$_3$) 1714, 1689, 1595 cm$^{-1}$
MS(FD): m/e 958 (M−1).

EXAMPLES 22 AND 23

2',4'-Di-O-acetyl-4''-azido-4''-deoxy-20-DH-20-O-phenyldesmycosin (Compound 24)

2',4'-Di-O-acetyl-4''-(2-methoxyethoxy)-20-DH-20-O-phenyl-desmycosin (Compound 43)

A solution of 2',4'-di-O-Ac-20-DH-20-O-Ph-4''-O-(trifluoromethanesulfonyl)-desmycosin (5.0 g, 4.70 mmol) and NaN$_3$ (1.55 g, 5 eq.) in dry DME (25 mL) was heated at 70° C. for 5 hr. under a nitrogen atmosphere. The reaction solution was diluted with deionized H$_2$O (250 mL), extracted with CH$_2$Cl$_2$ (3×75 mL), dried (Na$_2$SO$_4$) and evaporated to give a white solid foam. The foam was chromatographed on a silica-gel flash column, using 1 L of ethyl acetate/hexane (1:1) followed by 750 mL of ethyl acetate/hexane (2:1) as the eluent. Appropriate fractions were combined to give the title compounds.

2',4'-Di-O-Ac-4''-azido-4''-deoxy-20-DH-20-O-Phdesmycosin:

UV (EtOH): $\lambda_{max}$ 279 nm ($\epsilon$23,222)
IR (CHCl$_3$): 2123, 2097, 1745 1714(sh), 1679, 1594 cm$^{-1}$
MS(FD): m/e 958 (M).

2',4'-Di-O-Ac-4''-(2-methoxyethoxy)-20-DH-20-O-Phdesmycosin:

UV (EtOH): $\lambda_{max}$279 nm ($\epsilon$21,803)
IR (CHCl$_3$): 1745, 1716(sh), 1678, 1593 cm$^{-1}$
$^1$H NMR (CDCl$_3$): $\delta$4.94 (dd, 2'-H, overlap with 15-H), 4.76 (dd, 4'-H), 3.37 (s, 3H), 2.95 (dd, 4''-H, overlap with 2''-H)
MS(FD) m/e 990 (M−1).

EXAMPLE 24

4''-Azido-4''-deoxy-20-DH-20-O-phenyl-desmycosin (Compound 25)

A solution of 2',4'-di-O-Ac-4''-azido-4'-deoxy-20-DH-20-O-Ph-desmycosin (710 mg, 0.74 mmol) in MeOH (15 mL) was allowed to stand at room temperature for 48 hr. The solution was evaporated to dryness to give the title compound as a pale-yellow solid foam.

UV (EtOH): $\lambda_{max}$ 279 nm ($\epsilon$22,552)
IR (CHCl$_3$): 2122, 2091, 1714, 1679, 1594 cm$^{-1}$
MS(FD): m/e 875 (M+H).

EXAMPLE 25

2',4'-Di-O-acetyl-4''-deoxy-20-DH-20-O-phenyl-4''-pyridinium-desmycosin (Compound 22)

A solution of 2',4'-di-O-Ac-20-DH-20-O-Ph-4''-O-(trifluoromethanesulfonyl)-desmycosin (2.50 g, 2.4 mmol) in pyridine (25 mL) was allowed to stand at room temperature with exclusion of moisture for 3 days. The solution was diluted with saturated NaHCO$_3$ solution (200 mL), extracted with CH$_2$Cl$_2$ (3×50 mL), dried Na$_2$SO$_4$) and evaporated to dryness to give the title compound as a yellow solid foam.

UV (EtOH): $\lambda_{max}$ 278 nm ($\epsilon$19,771)
IR (CHCl$_3$) 1745, 1718(sh), 1679, 1594 cm$^{-1}$
$^1$H NMR (CDCl$_3$) $\delta$9.13 (d, 2H), 8.52 (t, 1H), 8.08 (dd, 2H)
MS(FD) m/e 994 (M).

EXAMPLE 26

2',4'-Di-O-acetyl-4''-deoxy-20-DH-20-O-phenyl-4''-(pyrrol-1-yl)-desmycosin (Compound 45)

A solution of 2',4'-di-O-Ac-20-DH-20-O-Ph-4''-O-(trifluoromethanesulfonyl)-desmycosin (2.14 g, 2.01 mmol) in pyrrole (10 mL) was allowed to stand at room temperature with the exclusion of moisture for 18 hr. The solution was dilueted with saturated NaHCO$_3$ solution (150 mL), extracted with CH$_2$Cl$_2$ (3×50 mL), dried (Na$_2$SO$_4$) and concentrated in vacuo to give a dark oil. The oil was chromatographed on a silica-gel flash column, using ethyl acetate/hexane (2:1) as the eluent, to give 344 mg (17%) of the title compound as a mixture of epimers at 4''.

UV (EtOH): $\lambda_{max}$ 279 nm ($\epsilon$23,093)
IR (CHCl$_3$): 1745, 1718(sh), 1680, 1593 cm$^{-1}$
$^1$H NMR (CDCl$_3$): $\delta$6.80–6.60 (m, 2-H), 6.14 (br, 1H), 5.97 (br, 1H)
MS(FD): m/e 982 (M).

EXAMPLE 27

4''-Deoxy-20-DH-20-O-phenyl-4''-pyrrol-1-yl-desmycosin (Compound 46)

A solution of 2',4'-di-O-Ac-4''-deoxy-20-DH-20-O-Ph-4''-(pyrrol-1-yl)-desmycosin (310 mg, 0.32 mmol) in MeOH (15 mL) was allowed to stand at room temperature for 48 hr. The solution was evaporated to dryness to give the title compound as a mixture of epimers at 4''

UV (EtOH): $\lambda_{max}$ 279 nm ($\epsilon$23,137)
IR (CHCl$_3$): 1712, 1677, 1593 CM$^{-1}$
$^1$H NMR (CDCl$_3$): $\delta$6.80–6.60 (m, 2H), 6.14 (m, 1H), 5.98 (m, 1H), 5.03 (d, 1''-H)
MS(FD): m/e 899 (M+H).

EXAMPLE 28

2',4'-Di-O-acetyl-4''-amino-4''-deoxy-20-DH-20-O-phenyldesmycosin (Compound 20)

A stream of dry NHs was bubbled into a solution of 2',4'-di-O-Ac-20-DH-20-O-Ph-4''-O-(trifluoromethanesulfonyl)-desmycosin (5.0 g, 4.70 mmol) in dry DME (70 mL) for 20 min. The reaction vessel was sealed and heated at 70° C. for 5 hr. The solution was diluted with deionized H$_2$O (250 mL), extracted with CH$_2$Cl$_2$ (4×100 mL), dried (Na$_2$SO$_4$) and evaporated to dryness to give a solid foam. The foam was chromatographed on a silica-gel flash column, using a 500-mL gradient of ethyl acetate→ethyl acetate/methanol (9:1) followed by 750 mL of ethyl acetate/methanol (9:1) as the eluent, to give 1.77 g (40.5%) of the title compound as a white solid foam.

UV (EtOH): $\lambda$max 279 nm ($\epsilon$22,867)
IR (CHCl$_3$) 1744, 1714(sh), 1678, 1594 cm$^{-1}$
$^1$H NMR (CDCl$_3$): $\delta$4.91 (dd, 2'-H, overlap with 15-H), 4.75 (dd, 4'-H), 2.39 (dd, 4''-H, overlap with 2-H)
MS(FD): m/e 932 (M).

EXAMPLE 29

4''-Amino-4''-deoxy-20-DH-20-O-phenyl-desmycosin Compound 21)

Method A:

A solution of 2',4'-di-O-Ac-4''-amino-4''-deoxy-20-DH-20-O-Ph-desmycosin (1.12 g, 1.20 mmol) in MeOH (25 mL) was allowed to stand at room temperature for 47 hr. The solution was evaporated to dryness to give a pale-yellow solid foam. The foam was chromatographed on a Waters Prep 500 LC (reverse-phase), using an 8-L gradient of 0.2M NaClO$_4$ solution→0.2M NaClO$_4$/acetonitrile (55:45) followed by 2 L of 0.2M NaClO$_4$/acetonitrile (55:45) as the eluent, to give 655 mg (64.3%) of the title compound as a white solid foam.

Method B:

A solution of 4''-O-hydroxyimino-20-DH-20-O-Ph-desmycosin (1.0 g, 1.2 mmol) and ammonium acetate (1.8 g) in MeOH (50 mL) was treated with NaBH$_3$CN (36 mg, 1.5 eq.). After a few minutes, a 20% aqueous TiCl$_3$ solution was added dropwise to the methanolic solution. The mixture was stirred for 1 hr. under a nitrogen atmosphere and then was diluted with saturated NaHCO$_3$ solution (200 mL). The resulting mixture was extracted with CH$_2$Cl$_2$ (4×50 mL), dried (Na$_2$SO$_4$) and evaporated to dryness. The residue was chromatographed on a silica-gel flash column, using a 1-L gradient of CH$_2$Cl$_2$→CH$_2$CL$_2$/MeOH/NH$_4$OH (90:10:0.5) followed by 1.5 L of CH$_2$Cl$_2$/MeOH/NH$_4$OH (90:10:0.5) as the eluent, to give 292 mg (29.7%) of the title compound.

UV (EtOH): $\lambda_{max}$ 279 nm ($\epsilon$22,308)
IR (CHCl$_3$): 1713, 1678, 1594 cm$^{-1}$
$^1$H NMR (CDCl$_3$): 2.38 (dd, 4''-H)
MS(FD): m/e 849 (M+H).

EXAMPLE 30

20-DH-4''-(2-Methoxyethoxy)-20-O-phenyl-desmycosin (Compound 44)

A solution of 2',4'-di-O-Ac-20-DH-4''-(2-methoxyethoxy)-20-O-Ph-desmycosin (150 mg, 0.1% mmol) in MeOH (15 mL) was allowed to stand at room temperature for 48 hr. The solution was evaporated to dryness to give the title compound as a colorless glass.

UV (EtOH): $\lambda_{max}$ 279 nm ($\epsilon$23,296)
IR (CHCl$_3$) 1714, 1678, 1593 cm$^{-1}$
$^1$H NMR (CDCl$_3$) $\delta$3.38 (s, 3H), 2.93 (dd, 4'-H, overlap with 2''-H)
MS(FD): m/e 908 (M+H).

EXAMPLE 31

4''-Benzylamino-4''-deoxy-20-DH-20-O-phenyl-desmycosin (Compound 47)

A solution of 2',4'-di-O-Ac-4''-amino-4''-deoxy-20-DH-20-O-Ph-desmycosin (1.0 g, 1.07 mmol) and benzaldehyde (440 $\mu$L, 4 eq.) in anhydrous MeOH (25 mL) over 4 Å molecular sieves was treated with NaBH$_3$CN (67 mg, 3 eq.) in one portion. The mixture was allowed to stand at room temperature for 16 hr. with the exclusion of moisture. The excess hydride was neutralized with 1N HCl, and the resulting solution was diluted with saturated NaHCO$_3$ solution (150 mL). The mixture was extracted with CH$_2$Cl$_2$ (4×50 mL), dried (Na$_2$SO$_4$) and concentrated to a colorless oil. The oil was chromatographed on a silica-gel flash column, using a 500-mL gradient of CH$_2$Cl$_2$→CH$_2$Cl$_2$/MeOH (9:1) followed by 500 mL of CH$_2$Cl$_2$/MeOH (9:1) as the eluent, to give 515 mg (51.2%) of the title compound as a colorless glass.

UV (EtOH): $\lambda_{max}$ 279 nm ($\epsilon$23,250)
IR (CHCl$_3$): 1713, 1678, 1592 cm$^{-1}$
$^1$H NMR (CDCl$_3$): $\delta$3.74 (d, 1H), 3.93 (d, 1H)
MS(FD): m/e 938 (M).

EXAMPLES 32–33

4''-Deoxy-20-DH-20-O-phenyl-4''-(n-propylamino)desmycosin (Compound 38)

4''-Deoxy-20-DH-20-O-phenyl-4''-[di-(n-propyl)amino]desmycosin (Compound 48)

Using the procedure described in Example 31, 2',4'-di-O-Ac-4''-amino-4''-deoxy-20-DH-20-O-Ph-desmycosin (1.0 g, 1.07 mmol), propionaldehyde (310 $\mu$L, 4 eq.) and sodium cyanoborohydride (67 mg, 3 eq.) were reacted. The product mixture was chromatographed on a silica-gel flash column, using a 1-L gradient of CH$_2$Cl$_2$→CH$_2$Cl$_2$/MeOH (9:1) followed by 1 L of CHzClz/MeOH (9:1) as the eluent, to give the title compounds.

4''-Deoxy-20-DH-20-O-Ph-4''-[di-(n-propyl)amino]-desmycosin:

UV (EtOH): $\lambda_{max}$ 279 nm ($\epsilon$23,320)
IR (CHCl$_3$): 1713, 1678, 1593 cm$^{-1}$
$^1$H NMR (CDCl$_3$): $\delta$1.39 (m, 4H), 0.85 (t, 6H)
MS(FD): m/e 932 (M).

4''-Deoxy-20-DH-20-O-Ph-4''-(n-propylamino)-desmycosin:

UV (EtOH): $\lambda_{max}$ 279 nm ($\epsilon$23,377)
IR (CHCl$_3$): 1713, 1678, 1593 cm$^{-1}$
$^1$H NMR (CDCl$_3$): $\delta$2.45 (dd, 4''-H, overlap with —NMe$_2$), 1.48 (m, 2H), 0.93 (t, overlap with 17-H)
MS(FD): m/e 891 (M+H).

EXAMPLE 34

4''-Deoxy-20-DH-20-O-phenyl-4''-(piperidin-1-yl)desmycosin (Compund 42)

This compound was prepared as described in Example 31 by reacting 2',4'-di-O-Ac-4''-amino-4''-deoxy-20-DH-20-O-Ph-desmycosin (760 mg, 0.82 mmol) with glutaraldehyde (51.2 mg, 1.5 eq.) and sodium cyanoborohydride (51 mg, 1.5 eq.). The product mixture was chromatographed on a silica-gel flash column, using a 1-L gradient of CH$_2$Cl$_2$→CH$_2$Cl$_2$/MeOH (9:1) followed by 500 mL of CH$_2$Cl$_2$/MeOH (9:1) as the eluent, to give 419 mg (56.1%) of the title compound as an opaque glass.

UV (EtOH): $\lambda_{max}$ 279 nm ($\epsilon$22,896)
IR (CHCl$_3$) 1713, 1678, 1593 cm$^{-1}$
$^1$H NMR (CDCl$_3$): $\delta$2.60 (br, 4H), 4.44 (dd, 4''-H)
MS(FD): m/e 916 (M).

EXAMPLE 35

4''-Deoxy-20-DH-4''-isopropylamino-20-O-phenyldesmycosin (Compound 35)

A solution of 2',4'-di-OAc-4''-amino-4''-deoxy-20-DH-20-O-Ph-desmycosin (968 mg, 1.04 mmol) and acetone (380 $\mu$L, 5 eq.) in anhydrous MeOH (25 mL) was treated with NaBH$_3$CN (65 mg, 3 eq.). The solution was allowed to stand for 3 days at room temperature with the exclusion of moisture. The reaction mixture was then evaporated to dryness. The residue was dissolved in ethyl acetate (75 mL) and extracted with 0.5M pH 6.5 phosphate buffer (2×50 mL). The organic layer was dried (Na$_2$SO$_4$) and evaporated to dryness to give the title compound.

UV (EtOH): $\lambda_{max}$ 279 nm ($\epsilon$22,293)
IR (CHC$_3$): 1712, 1678, 1592 cm$^{-1}$
$^1$H NMR (CDCl$_3$): $\delta$2.86 (m, 1H), 2.43 (dd, 4''-H), 1.00 (d, overlap with 18-H)
MS(FD): m/e 890 (M).

EXAMPLES 36–39

4''-Deoxy-20-DH-4''-dimethylamino-20-O-phenyl-desmycosin (Compound 33)

4''-[(Cyanomethyl)methylamino]-4''-deoxy-20-DH-20-O-phenyl-desmycosin (Compound 29)

4''-Deoxy-20-DH-4''-methylamino-20-O-phenyl-desmycosin (Compound 31)

4''-(Cyanomethyl)amino-4''-deoxy-20-DH-20-O-phenyl-desmycosin (Compound 27)

A solution of 2',4'-di-O-Ac-4''-amino-4''-deoxy-20-DH-20-O-Ph-desmycosin (1.0 g, 1.07 mmol) and paraformaldehyde (97 mg, 3 eq.) in anhydrous MeOH (75 mL) was allowed to stand at room temperature with the exclusion of moisture. After 16 hr., NaBH$_3$CN (67 mg, 1.5 eq.) was added to the solution in one portion. After an additional 16 hr., the solution was evaporated to dryness. The residue was dissolved in ethyl acetate (75 mL) and extracted with 0.5M PH 6.5 phosphate buffer (1×50 mL). The aqueous layer was discarded. The organic layer was extracted with 0.5M pH 4.5 phosphate buffer (3×50 mL), dried (Na$_2$SO$_4$) and evaporated to dryness to give a mixture of compounds 27 and 28.

The aqueous extract was adjusted to pH 7.0 with 1N NaOH and then was extracted with ethyl acetate (3×50 mL). The ethyl acetate extract was dried (Na$_2$SO$_4$) and evaporated to dryness. The residue was chromatographed on a silica-gel flash column, using a 1-L gradient of CH$_2$Cl$_2$→CH$_2$Cl$_2$/MeOH (9:1) followed by 500 mL of CH$_2$Cl$_2$/MeOH (9:1) as the eluent, to give 327 mg (34.8%) of compound 33 as a white solid foam.

The mixture of compounds 27 and 28 was chromatographed on a Waters Prep 500 LC (reverse-phase, C-18), using an 8-L gradient of 0.2M NaClO$_4$ solution/acetonitrile (4:1)→0.2M NaClO$_4$/acetonitrile (2:3) followed by 2L of 0.2M NaClO$_4$/acetonitrile (2:3) as the eluent. Fractions were combined on the basis of analytical HPLC to give 120 mg of compound 27 and 169 mg of a mixture of compounds 28 and 31 (72:28).

The mixture of compounds 28 and 31 was dissolved in 1N H$_2$SO$_4$ (10 mL) and allowed to stand at room temperature for 4 days. The solution was made basic with saturated NaHCO$_3$ solution (100 mL) and extracted with CH$_2$Cl$_2$ (3×25 mL). The CH$_2$Cl$_2$ extracts were dried (Na$_2$SO$_4$) and evaporated to dryness to give compound 31.

4''-Deoxy-20-DH-4''-dimethylamino-20-O-Ph-desmycosin:

UV (EtOH): $\lambda_{max}$ 279 nm ($\epsilon$23,063)
IR (CHCl$_3$): 1713, 1678, 1593 cm$^{-1}$
$^1$H NMR (CDCl$_3$): $\delta$ 2.41 (s, 6H)
MS(FD): m/e 876 (M).

4''-(Cyanomethyl)amino-4''-deoxy-20-DH-20-O-Ph-desmycosin:

UV (EtOH): $\lambda_{max}$ 279 nm ($\epsilon$22,011)
IR (CHCl$_3$): 2460 (w), 1715, 1679, 1595 cm$^{-1}$
$^1$H NMR (CDCl$_3$): $\delta$3.69 (d, 1H), 3.51 (d, 1H), 2.27 dd, 4''-H)
MS(FD): m/e 888 (M+H).

4''-[(Cyanomethyl)methylamino-4''-deoxy-20-DH-20-O-Ph-desmycocin:

UV (EtOH): $\lambda_{max}$ 279 nm ($\epsilon$23,622)
IR (CHCl$_3$): 2460 (w), 1713, 1677, 1593 cm$^{-1}$
$^1$H NMR (CDCl$_3$): $\delta$2.28 (dd, 4''-H)
MS(FD): m/e 901 (M).

4''-Deoxy-20-DH-4''-methylamino-20-O-Ph-desmycosin:

UV (EtOH): $\lambda_{max}$ 279 nm ($\epsilon$21,781)
IR (CHCl$_3$): 1713, 1678, 1594 cm$^{-1}$
$^1$H NMR (CDCl$_3$): $\delta$2.37 (s, 3H), 2.04 (dd, 4''-H)
MS(FD): m/e 863 (M+H).

EXAMPLE 40

4''-Acetylamino-4''-deoxy-20-DH-20-O-phenyl-desmycosin (Compound 37)

A solution of 2',4'-di-O-Ac-4''-amino-4''-deoxy-20-DH-20-O-Ph-desmycosin (1.0 g, 1.07 mmol) and acetic anhydride (111 $\mu$L, 1.1 eq.) in MeOH (50 mL) was allowed to stand at room temperature for 48 hr. The reaction solution was concentrated in vacuo to a pale-yellow oil. The oil was diluted with CH$_2$Cl$_2$ (100 mL) and then extracted with saturated NaHCO$_3$ solution (2×100 mL) and deionized H$_2$O (100 mL). The CH₂Cl₂ solution was dried (Na₂SO₄) and evaporated to dryness to give the title compound as a solid foam.

UV (EtOH): λ$_{max}$ 279 nm (ε19,521)
IR (CHCl₃): 3440, 1715, 1674, 1594 cm$^{-1}$
¹H NMR (CDCl₃): δ4.86 (dd, 4''-H), 2.02 (s, 3H)
MS(FD): m/e 891 (M+H).

EXAMPLE 41

2',4'-Di-O-acetyl-4''-deoxy-3''-oxo-20-DH-O-phenyl-lactenocin (Compound 51)

Alternate Method

A solution of 2',4'-di-O-Ac-20-DH-20-O-Ph-4''-O-(trifluoromethanesulfonyl)-lactenocin (250 mg, 0.24 mmol) and DBU (0.07 mL, 2 eq.) in tetrahydrofuran was allowed to stand at room temperature with the exclusion of moisture. After 20 hours, the solution was concentrated in vacuo. The residue was diluted with CH₂Cl₂ (50 mL), washed with saturated NaHCO₃ solution (2×25 mL), and dried (Na₂SO₄). The residue can be chromatographed as described in Examples 19-20 to give the title compound.

We claim:

1. A compound of the formula:

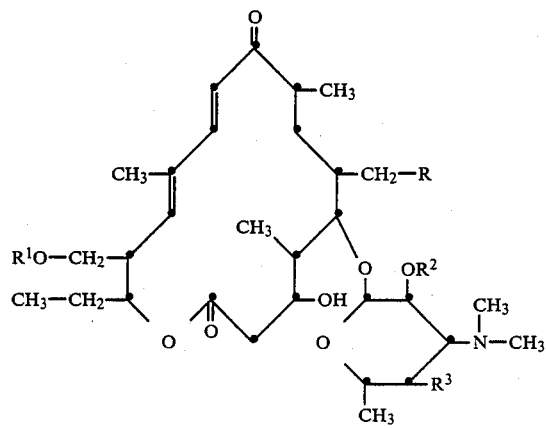

wherein
R is CH₂Z,

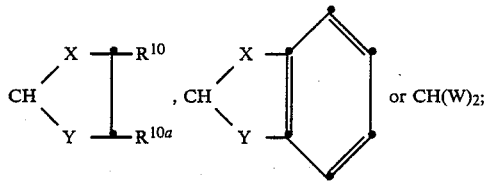

Z is hydrogen, halo, OR⁴, SR⁵, N₃ or NR⁶R⁷;
X and Y independently represent O, S, N-CH₃, N-phenyl or N-benzyl;
W is O(C₁-C₄-alkyl), S-phenyl or S-(R¹¹-substituted-phenyl);
R¹ is

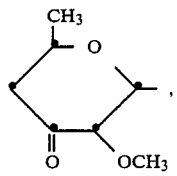 (a)

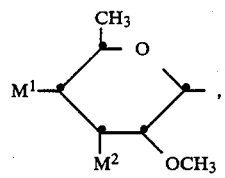 (b)

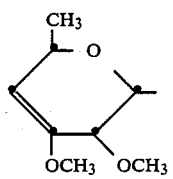 (c)

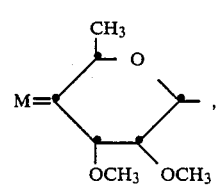 (d)

wherein
M is O, NOR$^{1a}$ or NH;
M¹ is halo, N₃, NR¹²R¹³, NH(C₁-C₄-alkanoyl), pyridinium, pyrrolyl, C₁-C₄-alkoxy, (C$_{1l}$ -C₃-alkoxy)-(C$_{1l}$ -C₃-alkoxy), OSO₂R$^{1b}$ or imidazolyl-thiocarbonyloxy;
M² is hydroxy or methoxy;
R$^{1a}$ is hydrogen, C₁-C₄-alkyl or C₁-C₄-alkyl having a C₁-C₃-alkoxy, (C₁-C₃-alkoxy)-(C₁-C₃-alkoxy), NR⁸R⁹ or (R⁸R⁹N)-(C₁-C₃-alkoxy) substituent;
R$^{1b}$ is C₁-C₄-alkyl, halo-substituted-C₁-C₄-alkyl, phenyl, benzyl, or phenyl or benzyl having from one to three C₁-C₃-alkyl, C₁-C₃-alkoxy or halo substituents;
R² is hydrogen, C₁-C₅-alkanoyl, halo-substituted-C₁-C₅-alkanoyl, or benzoyl, phenylacetyl or phenylpropionyl, each of which may have an R¹¹ substituent on the phenyl ring;
R³ is hydrogen, OR² or mycarosyloxy;
R⁴ is C₁-C₄-alkyl; C₁-C₄-alkanoyl; cyclohexyl; phenyl, benzyl, phenethyl or phenoxyethyl each of which may have an R11 substituent on the ring; or a heteroaryl group selected from pyridinyl, pyrimidinyl, pyridazinyl or pyrazinyl;
R⁵ is C₁-C₄-alkyl; cyclohexyl; phenyl, benzyl or phenethyl, each of which may have an R¹¹ substituent on the phenyl ring; or a heteroaryl group selected from pyridinyl, tetrazolyl, oxazolyl or thiazolyl;
R⁶ and R⁷ independently are hydrogen, C₁-C₈-alkyl or a group of the formula:

(CH₂)$_n$(Cyc)

where n is 0, 1 or 2, and Cyc is C₃-C₈-cycloalkyl, phenyl or R¹¹-substituted phenyl; or taken together with the adjacent nitrogen atom form a saturated or unsaturated heterocyclic monocyclic ring containing from 5 to 16 ring atoms or a bicyclic or tricyclic ring system containing from 8 to 20 ring atoms wherein one or more of the ring atoms may be substituted by C₁-C4-alkyl, C₁-C4-alkoxy, C₁-C4-alkoxycarbonyl, hydroxy, C₁-C4- alkanoyloxy, halo, $NR^8R^9$, phenyl or $R^{11}$-substituted phenyl;

$R^8$ and $R^9$ independently are $C_1$-$C_4$-alkyl or $(CH_2)_n(Cyc)$; or taken together with the adjacent nitrogen atom form a saturated heterocyclic monocyclic ring containing from 5 to 8 ring atoms;

$R^{10}$ and $R^{10a}$ independently are hydrogen, methyl, phenyl, methoxycarbonyl, ethoxycarbonyl or phenoxycarbonyl; and $R^{11}$ is halo, $C_1$-$C_3$-alkyl, $C_1$-$C_3$-alkoxy, nitro or hydroxy; and $R^{12}$ and $R^{13}$ independently are hydrogen, cyanomethyl, $C_1$-$C_4$-alkyl or $(CH_2)_n(Cyc)$; or taken together with the adjacent nitrogen atom form a saturated heterocyclic monocyclic ring containing from 5 to 8 ring atoms;

and the acid addition salts of these compounds.

2. A compound of claim 1 wherein R is $CH_2Z$, and Z has the meaning defined in claim 1.

3. A compound of claim 1 wherein R is

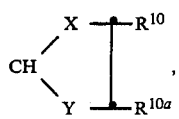

and $R^{10}$ and $R^{10a}$ are as defined in claim 1.

4. A compound of claim 1 wherein R is

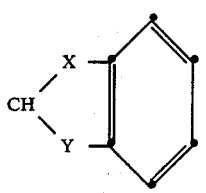

and X and Y are as defined in claim 1.

5. A compound of claim 1 wherein R is $CH(W)_2$, and W is as defined in claim 1.

6. A compound of claim 1 wherein Z is $OR^4$, and $R^4$ is as defined in claim 1.

7. A compound of claim 1 wherein Z is $SR^5$, and $R^5$ is as defined in claim 1.

8. A compound of claim 2 wherein Z is halo or $N_3$.

9. A compound of claim 2 wherein Z is hydrogen.

10. A compound of claim 1 wherein Z is $NR^6R^7$, and $R^6$ and $R^7$ are as defined in claim 1.

11. A compound of claim 6 wherein $R^4$ is $C_1$-$C_4$-alkyl, $C_1$-$C_4$-alkanoyl or cyclohexyl.

12. A compound of claim 1 wherein $R^4$ is phenyl, benzyl, phenethyl or phenoxyethyl, each of which may have an $R^{11}$ substituent on the ring, and $R^{11}$ is as defined in claim 1.

13. A compound of claim 12 wherein $R^4$ is phenyl.

14. A compound of claim 1 wherein $R^4$ is a heteroaryl group as defined in claim 1.

15. A compound of claim 7 wherein $R^5$ is $C_1$-$C_4$-alkyl or cyclohexyl.

16. A compound of claim 1 wherein $R^5$ is phenyl, benzyl or phenethyl, each of which may have an $R^{11}$ substituent on the phenyl ring, and $R^{11}$ is as defined in claim 1.

17. A compound of claim 1 wherein $R^5$ is a heteroaryl group as defined in claim I.

18. A compound of claim 1 wherein $R^6$ and $R^6$ independently are hydrogen, $C_1$-$C_8$-alkyl, or a group of the formula $(CH_2)_n(Cyc)$, and n and Cyc are as defined in claim 1.

19. A compound of claim 18 wherein $R^6$ and $R^7$ are $C_1$-$C_8$-alkyl.

20. A compound of claim 1 wherein $R^6$ and $R^7$ together with the adjacent nitrogen atom form a monocyclic ring as defined in claim 1 which may be substituted by $C_1$-$C_4$-alkyl, $C_1$-$C_4$-alkoxycarbonyl, hydroxy, $C_1$-$C_4$-alkanoyloxy, halo, $NR^8R^9$, pheny or $R^{11}$-substituted phenyl; and $R^8$, $R^9$ and $R^{11}$ are as defined in claim 1.

21. A compound of claim 20 wherein the monocyclic ring is piperidinyl or substituted piperidinyl.

22. A compound of claim 21 wherein the $NR^6R^7$ group is 3,5-dimethylpiperidin-1-yl.

23. A compound of claim 1 wherein $R^6$ and $R^7$ together with the adjacent nitrogen atom form a bicyclic or tricyclic ring system as defined in claim 1.

24. A compound of claim 1 wherein $R^1$ is an (a) moiety as defined in claim 1.

25. A compound of claim 1 wherein $R^1$ is a (b) moiety as defined in claim 1.

26. A compound of claim 1 wherein $R^1$ is a (c) moiety as defined in claim 1.

27. A compound of claim 1 wherein $R^1$ is a moiety as defined in claim 1.

28. A compound of claim 20 wherein the ring is 3,5-dimethylpiperidin-1-yl.

29. A composition useful for treating susceptible bacterial infections and infections caused by susceptible Mycoplasma species comprising an effective amount of a compound of claim 1 and a suitable pharmaceutical vehicle.

30. A method for treating infections caused by susceptible bacteria which comprises administering an effective amount of a composition of claim 29 to an animal.

31. A method for treating infections caused by susceptible Mycoplasma species which comprises administering an effective amount of a composition of claim 29 to an animal.

* * * * *

UNITED STATES PATENT AND TRADEMARK OFFICE
CERTIFICATE OF CORRECTION

PATENT NO. : 4,920,103
DATED : April 24, 1990
INVENTOR(S) : Herbert A. Kirst et al.

It is certified that error appears in the above-identified patent and that said Letters Patent is hereby corrected as shown below:

In claim 1:
Column 28, line 30, "$(C_1 -C_3\text{-alkoxy})-(C_1 -C_3\text{-alkoxy})$," should read -- $(C_1-C_3\text{-alkoxy})-(C_1-C_3\text{-alkoxy})$ --.

Column 28, line 47, "R11" should read -- $R^{11}$ --.

Column 28, line 67, "$C_1$-C4-alkyl, $C_1$-C4-alkoxy," should read -- $C_1-C_4$-alkyl, $C_1-C_4$-alkoxy, --.

Column 28, line 68, "$C_1$-C4-alkoxycarbonyl, hydroxy, $C_1$-C4-" should read -- $C_1-C_4$-alkoxycarbonyl, hydroxy, $C_1-C_4$- --.

In claim 20:
Column 30, line 23, "$C_1-C_4$-alkyl, $C_1-C_4$-alkoxycarbonyl," should read -- $C_1-C_4$-alkyl, $C_1-C_4$-alkoxy, $C_1-C_4$-alkoxycarbonyl, --.

Column 30, line 24, "pheny" should read -- phenyl --.

In claim 27:
Column 30, line 40, "is a moiety" should read -- is a (d) moiety --.

Signed and Sealed this

Twenty-third Day of July, 1991

Attest:

HARRY F. MANBECK, JR.

Attesting Officer

Commissioner of Patents and Trademarks